US012630884B2

(12) United States Patent
Mizrahi

(10) Patent No.: US 12,630,884 B2
(45) Date of Patent: May 19, 2026

(54) METHOD OF SELECTING RUMINATING ANIMALS FOR A DESIRABLE HEREDITABLE TRAIT

(71) Applicants: The State of Israel, Ministry of Agriculture & Rural Development, Agricultural Research Organization (ARO) (Volcani Center), Rishon-LeZion (IL); The National Institute for Biotechnology in the Negev Ltd., Beer-Sheva (IL)

(72) Inventor: Itzhak Mizrahi, Tel-Aviv (IL)

(73) Assignees: The State of Israel, Ministry of Agriculture & Rural Development, Agricultural Research Organization (ARO) (Volcani Center), Rishon-LeZion (IL); The National Institute for Biotechnology in the Negev Ltd., Beer-Sheva (IL)

( * ) Notice: Subject to any disclaimer, the term of this patent is extended or adjusted under 35 U.S.C. 154(b) by 376 days.

(21) Appl. No.: 16/636,664

(22) PCT Filed: Aug. 6, 2018

(86) PCT No.: PCT/IL2018/050868
§ 371 (c)(1),
(2) Date: Feb. 5, 2020

(87) PCT Pub. No.: WO2019/030752
PCT Pub. Date: Feb. 14, 2019

(65) Prior Publication Data
US 2020/0248237 A1     Aug. 6, 2020

Related U.S. Application Data

(60) Provisional application No. 62/541,731, filed on Aug. 6, 2017.

(51) Int. Cl.
*C12Q 1/689*     (2018.01)
*A01K 67/02*     (2006.01)

(52) U.S. Cl.
CPC .............. *C12Q 1/689* (2013.01); *A01K 67/02* (2013.01); *A01K 2227/101* (2013.01); *C12Q 2600/124* (2013.01); *C12Q 2600/158* (2013.01)

(58) Field of Classification Search
CPC .. C12Q 2600/124; C12Q 1/689; A01K 67/02; A01K 2227/101
See application file for complete search history.

(56) References Cited

U.S. PATENT DOCUMENTS

2020/0123588 A1     4/2020    Mizrahi

FOREIGN PATENT DOCUMENTS

WO     WO 2017/187433     11/2017
WO     WO 2019/030752     2/2019

OTHER PUBLICATIONS

Ben Shabat et al., Specific microbiome-dependent mechanisms underlie the energy harvest efficiency of ruminants, The ISME J., vol. 10, pp. 2958-2972, supplemental material, pp. 1-27 (Year: 2016).*

Clemmons, B.A. et al., Altering the Gut Microbiome of Cattle: Considerations of Host-Microbiome Interactions for Persistent Microbiome Manipulation, Microbial Ecology, vol. 77, pp. 523-536 (Year: 2019).*

Clemmons, B.A. et al., Altering the Gut Microbiome of Cattle: Considerations of Host-Microbiome Interactions for Persistent Microbiome Manipulation, Microbial Ecology, vol. 77, pp. 523-536 Epub Jul. 22, 2018. (Year: 2019).*

Roehe et al. Bovine Host Genetic Variation Influences Rumen Microbial Methane Production with Best Selection Criterion for Low Methane Emitting and Efficiently Feed Converting Hosts Based on Metagenomic Gene Abundance. PLoS Genet. Feb. 18, 2016; PMID: 26891056 (Year: 2016).*

Shabat et al. Specific microbiome-dependent mechanisms underlie the energy harvest efficiency of ruminants. ISME J. Dec. 2016; 10(12):2958-2972. doi: 10.1038/ismej.2016.62. Epub May 6, 2016. PMID: 27152936; PMCID: PMC5148187 (Year: 2016).*

Sasson et al. Heritable Bovine Rumen Bacteria Are Phylogenetically Related and Correlated with the Cow's Capacity To Harvest Energy from Its Feed. mBio. Aug. 15, 2017;8(4):e00703-17. doi: 10.1128/mBio.00703-17. PMID: 28811339; PMCID: PMC5559629. (Year: 2017).*

Roehe et al. Bovine Host Genetic Variation Influences Rumen Microbial Methane Production with Best Selection Criterion for Low Methane Emitting and Efficiently Feed Converting Hosts Based on Metagenomic Gene Abundance. PLoS Genet. Feb. 18, 2016 (Year: 2016).*

GenBank (Accession KP106853) (Year: 2015).*

Henderson et al. Rumen microbial community composition varies with diet and host, but a core microbiome is found across a wide geographical range. Sci Rep 5, 14567 (Year: 2015).*

Ryan Goodman, Bull Semen Collection and Ohio Select Sires; beefrunner.com; published on Oct. 29, 2012 (Year: 2012).*

International Preliminary Report on Patentability Dated Feb. 20, 2020 From the International Bureau of WIPO Re. Application No. PCT/IL2018/050868. (7 Pages).

International Search Report and the Written Opinion Dated Oct. 22, 2018 From the International Searching Authority Re. Application No. PCT/IL2018/050868. (10 Pages).

Kruger Ben Shabat et al. "Specific Microbiome-Dependent Mechanisms Underlie the Energy Harvest Efficiency of Ruminants", The ISME Journal, 10(12): 2958-2972, Published Online May 6, 2016.

Sasson et al. "Heritable Bovine Rumen Bacteria Are Phylogenetically Related and Correlated With the Cow's Capacity to Harvest Energy From Its Feed", MBio, 8(4): e00703-17-1-e00703-17-12, Published Online Aug. 15, 2017.

(Continued)

*Primary Examiner* — Aaron A Priest
*Assistant Examiner* — Tian Yu

(57) ABSTRACT

A method of selecting a ruminating animal having a desirable, hereditable trait is disclosed. The method comprises analyzing in the microbiome of the animal for an amount of a hereditable microorganism which is associated with the hereditable trait, wherein the amount of the hereditable microorganism is indicative as to whether the animal has a desirable hereditable trait.

5 Claims, 12 Drawing Sheets

Specification includes a Sequence Listing.

(56)                    References Cited

OTHER PUBLICATIONS

Notice of Reasons for Rejection Dated Jun. 7, 2022 From the Japan Patent Office Re. Application No. 2020-528542 and Its Translation Into English. (9 Pages).

Huo et al. "Uncultured Bacterium Clone XJC39 16S Ribosomal RNA Gene, Partial Sequence", Database NCBI [Online], GenBank: GU174032.1, Database Accession No. GU174032, Nov. 29, 2009.

Supplementary European Search Report and the European Search Opinion Dated Apr. 7, 2021 From the European Patent Office Re. Application No. 18845065.4. (10 Pages).

De Barbieri et al. "Production Attributes of Merino Sheep Genetically Divergent for Wool Growth Are Reflected in Differing Rumen Microbiotas", Livestock Science, 178: 119-129, Aug. 2015.

Jami et al. "Similarity of the Ruminal Bacteria Across Individual Lactating Cows", Anaerobe, XP028520212, 18(3): 338-343, Available Online Apr. 21, 2012.

Lima et al. "Prepartum and Postpartum Rumen Fluid Microbiomes: Characterization and Correlation With Production Traits in Dairy Cows", Applied and Environmental Microbiology, XP055788364, 81(4): 1327-1337, Published Online Dec. 12, 2014.

Notification About Necessity to Submit Additional Materials Dated Jul. 20, 2022 From The Eurasian Patent Organization, The Eurasian Patent Office Re. Application No. 202090447 and its Translation into English. (7 Pages).

English Translation Dated Jan. 3, 2022 of Office Action Dated Nov. 8, 2012 From the Department of Intellectual Property (DIP), Ministry of Commerce of Thailand, Federal Institute of Industrial Property, Re. Application No. 2001000702. (2 Pages).

Notification About Necessity to Submit Additional Materials Dated Oct. 29, 2021 From The Eurasian Patent Organization, The Eurasian Patent Office Re. Application No. 202090447 and its Translation into English. (7 Pages).

Office Action Dated Nov. 8, 2012 From the Department of Intellectual Property (DIP), Ministry of Commerce of Thailand, Federal Institute of Industrial Property, Re. Application No. 2001000702 together with an English Summary. (3 Pages).

Grounds of Reason of Rejection Dated May 15, 2023 From the Korean Intellectual Property Office Re. Application No. 10-2020-7006732. (3 Pages).

Translation Dated May 26, 2023 of Grounds of Reason of Rejection Dated May 15, 2023 From the Korean Intellectual Property Office Re. Application No. 10-2020-7006732. (3 Pages).

English Summary Dated Mar. 9, 2023 of Notification of Office Action Dated Feb. 25, 2023 From the State Intellectual Property Office of the People's Republic of China Re. Application No. 201880064323.3. (2 pages).

Notice of Reasons for Rejection Dated Feb. 9, 2023 From the Japan Patent Office Re. Application No. 2020-528542 and Its Translation Into English. (10 Pages).

Notification of Office Action and Search Report Dated Feb. 25, 2023 From the State Intellectual Property Office of the People's Republic of China Re. Application No. 201880064323.3. (8 Pages).

Examination Report Dated May 20, 2024 From the Instituto Mexicano de la Propiedad Industrial, Secretaria de Economia, Direccion Divisional de Patentes Re. Application No. MX/a/2020/001400 and Its Translation Into English. (12 Pages).

Grounds of Reason of Rejection Dated May 31, 2024 From the Korean Intellectual Property Office Re. Application No. 10-2020-7006732 and Its Machine Translation Into English. (8 Pages).

Decision on Rejection Dated Sep. 5, 2023 From the State Intellectual Property Office of the People's Republic of China Re. Application No. 2020-528542 and Its Translation Into English. (8 Pages).

Examination Report Dated Feb. 2, 2024 From the Australian Government, IP Australia Re. Application No. 2018315764. (5 Pages).

Examination Report Dated Sep. 18, 2023 From the Instituto Mexicano de la Propiedad Industrial, Secretaria de Economia, Direccion Divisional de Patentes Re. Application No. MX/a/2020/001400 and Its Translation Into English. (8 Pages).

Notification of Office Action and Search Report Dated Dec. 25, 2023 From the State Intellectual Property Office of the People's Republic of China Re. Application No. 201880064323.3. (5 Pages).

Notification of Office Action Dated Apr. 11, 2024 From the State Intellectual Property Office of the People's Republic of China Re. Application No. 201880064323.3. (4 Pages).

Notification on Substantive Examination Dated Aug. 31, 2023 From the Ministry of Science and Technology, The National Office of Intellectual Property, NOIP of the Socialist Republic of Vietnam Re. Application No. 1-2020-01209 and Its Translation Into English. (4 Pages).

Office Action Dated Sep. 14, 2023 From the Israel Patent Office Re. Application No. 272531. (5 Pages).

Translation Dated May 2, 2024 of Notification of Office Action Dated Apr. 11, 2024 From the State Intellectual Property Office of the People's Republic of China Re. Application No. 201880064323. 3. (4 Pages).

Translation Dated Jan. 11, 2024 of Notification of Office Action and Search Report Dated Dec. 25, 2023 From the State Intellectual Property Office of the People's Republic of China Re. Application No. 201880064323.3. (2 Pages).

Office Action Dated Mar. 31, 2025 From the Israel Patent Office Re. Application No. 272531. (3 Pages).

Notice of Reason(s) for Rejection Dated Sep. 26, 2025 From the Japan Patent Office Re. Application No. 2020-528542. (9 pages).

Adler et al. "Video Article: Infinium Assay for Large-scale SNP Genotyping Applications", Journal of Visualized Experiments, 81:e50683, pp. 1-10, Nov. 19, 2013.

Benson et al. "Individuality in Gut Microbiota Composition is a Complex Polygenic Trait Shaped by Multiple Environmental and Host Genetic Factors", PNAs, 107(44): 18933-18938, Nov. 2, 2010.

Jami et al. "Exploring the Bovine Rumen Bacterial Community from Birth to Adulthood", The ISME Journal, 7(6): 1069-1079, Feb. 21, 2023.

Kruger et al. "Specific Microbiome-Dependent Mechanisms Underlie the Energy Harvest Efficiency of Ruminants", The ISME Journal, 10: 2958-2972, May 6, 2016.

Stevenson et al. "Dominance of Prevotella and Low Abundance of Classical Ruminal Bacterial Species in the Bovine Rumen Revealed by Relative Quantification Real-Time PCR", Applied Microbial and Cell Physiology, 75: 165-174, May 1, 2007. Abstract.

Yang et al. "GCTA: A Tool for Genome-wide Complex Trait Analysis", The American Journal of Human Genetics, 88: 76-82, Jan. 7, 2011.

Examination Report Under Sections 12 & 13 of the Patents Act, 1970 and the Patents Rules, 2003 Dated Oct. 22, 2025 From the Government of India, Intellectual Property India, Patents, Designs, Trade Marks, Geographical Indications, The Patent Office Re. Application No. 202027008394. (6 pages).

Jami et al. "Potential Role of the Bovine Rumen Microbiome in Modulating Milk Composition and Feed Efficiency", PLoS One 9(1): e85423, pp. 1-6, Jan. 22, 2014.

Li et al. "Metatranscriptomic Profiling Reveals Linkages between the Active Rumen Microbiome and Feed Efficiency in Beef Cattle", Applied and Environmental Microbiology, 83(9): e00061-17, pp. 1-6, Apr. 17, 2017.

Myer et al. "Rumen Microbiome from Steers Differing in Feed Efficiency", PLoS One 10(6): e0129174, pp. 1-17, Jun. 1, 2015.

* cited by examiner

SEQUENCE LISTING

```
<160> NUMBER OF SEQ ID NOS: 24

<210> SEQ ID NO 1
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 1
tgaggaatat tggtcaatgg acggaagtct gaaccagcca tgccgcgtga aggaagaatg      60
ccctatgggt tgtaaacttc ttttgccgca gagtaataag gggcgtgcgc gccccgatga     120
gagtatgcgg cgaataagca tcggctaact ccgtgccagc agccgcggta atacggagga     180
tgcgagcgtt atccggattt attgggttta aagggtgcgc aggcggacag ctaagtcagc     240
ggtgaaatat                                                            250

<210> SEQ ID NO 2
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 2
tgaggaatat tggacaatgg ccgagaggct gatccagcca tgccgcgtgc gggaagacgg      60
ccctatgggt tgtaaaccgc ttttgtcggg gagcaataag gtccacgcgt ggactgatga     120
gagtacctgg cgaataagca tcggctaact ccgtgccagc agccgcggta atacggagga     180
tgcaagcgtt atccggattt attgggttta aagggtgcgt aggcggcgag gtaagcgtga     240
ggtgaaagct                                                            250

<210> SEQ ID NO 3
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 3
tggggaatat tgggcaatgg ggggaaccct gacccagcaa cgccgcgtgg aggaagaagg      60
tcttcggatc gtaaactcct gtcctaagag acgagcagga gacggtaact taggaggaag     120
ccccggctaa ctacgtgcca gcagccgcgg taatacgtag ggggcaagcg ttgtccggaa     180
tgattgggcg taaagggcgc gtaggcggcc gcagaagtct gaagtgaaat acccgctttc     240
aaggtgggta                                                            250
```

```
<210> SEQ ID NO 4
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 4
tgaggaatat tggtcaatgg gcggaagcct gaaccagcca tgccgcgtgt gggaagaagg      60
ccctatgggt tgtaaaccac ttttagccgg gagtaataag gggcgtgcgc gccccgatga     120
gagtaccggc ggaataagca tcggctaact ccgtgccagc agccgcggta atacggagga     180
tgcaagcgtt atccggattt attgggttta aagggtgcgt aggcggaccg ttaagtcagc     240
ggtgaaaggt                                                            250

<210> SEQ ID NO 5
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 5
tgaggaatat tggtcaatgg acggaagtct gaaccagcca tgccgcgtgc gggaagacgg      60
ccctatgggt tgtaaaccgc ttttccccgg gagtaataag gcccgtgcgc gggccgatga     120
gagtaccggg ggaataagca tcggctaact ccgtgccagc agccgcggta atacggagga     180
tgcaagcgtt atccggattt attgggttta aagggtgcgt aggcggaccg ttaagtcagc     240
ggtgaaatgt                                                            250

<210> SEQ ID NO 6
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 6
tggggaatat tgggcaatgg gcgaaagcct gacccagcaa cgccgcgtga gtgaagaagg      60
ccttcgggtt gtaaagctct gttatagttg acgaaggaag tgacggtagg ctataaggaa     120
gccccggcta actacgtgcc agcagccgcg gtaatacgta gggggcgagc gttgtccgga     180
atgactgggc gtaaagggcg tgtaggcggt catttaagtc tggagtgaaa gtcctgcatt     240
caatgtggga                                                            250

<210> SEQ ID NO 7
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 7
tggggaatct tccgcaatgg gcgcaagcct gacggagcaa cgccgcgtgg gtgaggaagt      60
tcttcggaac gtaaagccct gttgtacatg acgaacgtgt atcctatcaa caacgggatg     120
caatgacggt agtgtacgag gaagccacgg ctaactacgt gccagcagcc gcggtaatac     180
```

-continued

```
gtaggtggca agcgttgtcc ggaattattg ggcgtaaagc gcatgtaggc ggtgatgtaa    240
gtctgtcgtg                                                           250
```

<210> SEQ ID NO 8
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 8

```
tgaggaatat tggacaatgg ccgagaggct gatccagcca tgccgcgtgc gggaagacgg     60
ccctatgggt tgtaaaccgc ttttgttgga gagcaataag agtcacgtgt gacttgatga    120
gagtatccag cgaataagca tcggctaact ccgtgccagc agccgcggta atacggagga    180
tgcgagcgtt atccggattt attgggttta aagggtgcgt aggcggatga ttaagcgtga    240
ggtgaaatgc                                                           250
```

<210> SEQ ID NO 9
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 9

```
tgaggaatat tggtcaatgg gcgagagcct gaaccagcca agtagcgtgc aggatgacgg     60
ccctatgggt tgtaaactgc ttttgcatgg gaataaagtg cgggacgcgt cccgttttgt    120
atgtaccatg agaataagga ccggctaatt ccgtgccagc agccgcggta atacggaagg    180
tccgggcgtt atccggattt attgggttta aagggagcgc aggctggaga ttaagcgtga    240
cgtgaaatgc                                                           250
```

<210> SEQ ID NO 10
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 10

```
tgaggaatat tggtcaatgg gcggaagcct gaaccagcca agtcgcgtga aggatgaagg     60
cattatgtgt tgtaaacttc tttagctgtg gagaaataag gtggtcgaga ccaccgatgc    120
tagtacacag agaataagga tcggctaact ccgtgccagc agccgcggta atacggagga    180
tccgagcgtt atccggattc attgggttta aagggtgcgc aggcggtgcc ttaagtcagc    240
ggtaaaatcg                                                           250
```

<210> SEQ ID NO 11
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 11

```
tgaggaatat tggtcaatgg gcggtagcct gaaccagcca agtcgcgtgc gggaagaagg     60
```

-continued

```
ccctacgggt cgtaaaccgc ttttgtcggg gagcaaagtg cgccacgtgt ggtgtattgc        120
gagtacccga agaaaaagca tcggctaact ccgtgccagc agccgcggta atacggagga        180
tgcgagcgtt atccggattt attgggttta aagggtgcgc aggcggcgcg tcaagtcagc        240
ggtcaaaatg                                                               250

<210> SEQ ID NO 12
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 12
ttcggcatat tggtcaatgg gcgcgagcct gaaccagcca agtagcgtgc aggatgacgg        60
ccctatgggt tgtaaactgc ttttatatag ggataaagtc ggggacgtgt ccccgtttgt        120
aggtactata tgaataagga ccggctaatt ccgtgccagc agccgcggta atacggaagg        180
tccgggcgtt atccggattt attgggttta aagggagcgc aggccggagg ctaagcgtga        240
cgtgaaatgt                                                               250

<210> SEQ ID NO 13
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 13
tgaggaatat tggacaatgg ccgaaaggct gatccagcca tgccgcgtgc gggaagacgg        60
ccctatgggt tgtaaaccgc ttttgttggg gagcaataag ggccacgtgt gacccgatga        120
gagtacccag cgaataagca tcggctaact ccgtgccagc agccgcggta atacggagga        180
tgcaagcgtt atccggattt attgggttta aagggtgcgt aggcggacga ttaagcgtga        240
ggtgaaatgc                                                               250

<210> SEQ ID NO 14
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 14
tgaggaatat tggtcaatgg gcggaagcct gaaccagcca agtagcgtga aggatgacgg        60
ccctacgggt tgtaaacttc ttttatgcgg gaacaaagtg cgccacgcgt ggcgttttgc        120
gcgtaccgca ggaaaaagca ccggctaatt ccgtgccagc agccgcggta atacggaagg        180
tgcgagcgtt atccggattc attgggttta aagggagcgt aggcggagcg ccaagtcagc        240
tgtgaaatcc                                                               250

<210> SEQ ID NO 15
<211> LENGTH: 250
<212> TYPE: DNA
<213> ORGANISM: Artificial sequence
<220> FEATURE:
<223> OTHER INFORMATION: operational taxonomic units (OTU) nucleic acid
```

-continued sequence

<400> SEQUENCE: 15
tggggaatat tgcacaatgg aggaaactct gatgcagcga cgccgcgtga gtgaagaagt      60
atttcggtat gtaaagctct atcagcaggg aagataatga cggtacctga ataagaagca     120
ccggctaaat acgtgccagc agccgcggta atacgtatgg tgcaagcgtt atccggattt     180
actgggtgta aagggagtgc aggcggtctg aaaagtcaga tgtgaaagcc cggggctcaa     240
ccccgggact                                                           250

<210> SEQ ID NO 16
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 16
tggggaatat tgcacaatgg gggaaaccct gatgcagcga cgccgcgtga gtgaagaagt      60
atttcggtat gtaaagctct atcagcaggg aagaaaatga cggtacctga ctaagaagcc     120
ccggctaact acgtgccagc agccgcggta atacgtaggg ggcaagcgtt atccggattt     180
actgggtgta aagggagcgc agacggaaga acaagtctga tgtgaaatgc gggggctcaa     240
ctcctgaatt                                                           250

<210> SEQ ID NO 17
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 17
tgaggaatat tggtcaatgg gcgagagcct gaaccagcca agtagcgtgc aggaagacgg      60
ccctatgggt tgtaaactgc ttttatatag ggataaagtc ggggacgtgt ccccgtttgt     120
aggtactata tgaataagga ccggctaatt ccgtgccagc agccgcggta atacggaagg     180
tccgggcgtt atccggattt attgggttta aagggagcgc aggccggctt ttaagcgtga     240
cgtgaaatgt                                                           250

<210> SEQ ID NO 18
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 18
tgaggaatat tggtcaatgg gcgcgagcct gaaccagcca agtagcgtgc aggatgacgg      60
ccctatgggt tgtaaactgc ttttggaggg gaataaagtc gtctacgtgt aggtgtttgc     120
atgtaccctc agaataagga ccggctaatt ccgtgccagc agccgcggta atacggaagg     180
tcctggcgtt atccggattt attgggttta aagggagcgc aggcgggcga ttaagcgtga     240
cgtgaaatgc                                                           250

<210> SEQ ID NO 19

<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 19
tgaggaatat tggtcaatgg ccgcgaggct gaaccagcca agtagcgtgc aggatgacgg      60
ccctctgggt tgtaaactgc ttttatgcgg gaacaaaggc gtctacgtgt agtcgtgtgc     120
gtgtaccgca ggaaaaagga ccggctaatt ccgtgccagc agccgcggta atacggaagg     180
tccgggcgtt atccggattt attgggttta aagggagcgc aggctgaagc gcaagccggc     240
tgtaaaattt                                                           250

<210> SEQ ID NO 20
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 20
tgaggaatat tggtcaatgg gcggaagcct gaaccagcca agtcgcgtga aggatgaagg      60
tattatgtat tgtaaacttc tttagctgtg gagaaataag gtgctcgtga gcaccgatgc     120
tagtacacag agaataaggg tcggctaact ccgtgccagc agccgcggta atacggagga     180
cccgagcgtt atccggattc attgggttta aagggtgcgc aggcggcttc ttaagtcagc     240
ggtaaaatcg                                                           250

<210> SEQ ID NO 21
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 21
tggggaatct tccgcaatgg gcgaaagcct gacggagcaa cgccgcgtga gtgaagaagg      60
tcttcggatc gtaaagctct gttgaagggg acgcacggcg cctgttacaa gatagcaggt     120
gaatgacggt acccttcgag gaagccacgg ctaactacgt gccagcagcc gcggtaatac     180
gtaggcggca agcgttgtcc ggaatcattg ggcgtaaagg gagcgcaggt ggacgtatag     240
gtccttctta                                                           250

<210> SEQ ID NO 22
<211> LENGTH: 250
<212> TYPE: DNA
<213> ORGANISM: Artificial sequence
<220> FEATURE:
<223> OTHER INFORMATION: operational taxonomic units (OTU) nucleic acid
      sequence

<400> SEQUENCE: 22
tggggaatat tgcacaatgg gggaaaccct gatgcagcga tgccgcgtgg aggaagaagg      60
ttttcggatt gtaaactcct gtcttaaagg acgataatga cggtacttta ggaggaagct     120
ccggctaact acgtgccagc agccgcggta atacgtaggg agcgagcgtt gtccggaatt     180
actgggtgta aagggagcgt aggcgggagt gcaagtcaga tgtgaaatac atgggctcaa     240

-continued

```
cccatgggct                                                      250

<210> SEQ ID NO 23
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 23
cctacgggag gcagcag                                              17

<210> SEQ ID NO 24
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 24
ccgtcaattc mtttragt                                             18
```

METHOD OF SELECTING RUMINATING ANIMALS FOR A DESIRABLE HEREDITABLE TRAIT

RELATED APPLICATIONS

This application is a National Phase of PCT Patent Application No. PCT/IL2018/050868 having International filing date of Aug. 6, 2018, which claims the benefit of priority under 35 USC § 119(e) of U.S. Provisional Patent Application No. 62/541,731 filed on Aug. 6, 2017. The contents of the above applications are all incorporated by reference as if fully set forth herein in their entirety.

SEQUENCE LISTING STATEMENT

The ASCII file, entitled 81379SequenceListing.txt, created on Feb. 5, 2020, comprising 12,784 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a method of selecting a ruminating animal for a desired hereditable trait based on the presence of particular bacteria in the microbiome thereof.

The bovine rumen microbiome essentially enables the hosting ruminant animal to digest its feed by degrading and fermenting it. In this sense this relationship is unique and different from the host-microbiome interactions that have evolved between in humans and non-herbivorous animals, where such dependence does not exist. This strict obligatory host-microbiome relationship, which was established approximately 50 million years ago, is thought to play a major role in host physiology. Despite its great importance, the impact of natural genetic variation in the host—brought about through sexual reproduction and meiotic recombination—on the complex relationship of rumen microbiome components and host physiological traits is poorly understood. It is known that associations between specific components of the rumen microbiome to animals physiology exist, mainly exemplified by the ability of the animal to harvest energy from its feed [Kruger Ben Shabat S, et al., 2016. ISME J 10:2958-2972].

These recent findings position the bovine rumen microbiome as the new frontier in the effort to increase the feed efficiency of milking cows. As human population is continually increasing this could have important implications for food security issues as an effort towards replenishing food sources available for human consumption while lowering environmental impact in global scale. Despite its great importance, the complex relationship of rumen microbiome components and host genetics and physiology is poorly understood.

Background art includes Guan L L, et al., 2008. FEMS Microbiology Letters 288:85-9; Roche R, et al., 2016. PLoS Genet 12:e1005846; Li Z, et al., 2016. Microbiology Reports 8:1016-102; and WO2017/187433.

SUMMARY OF THE INVENTION

According to an aspect of the present invention there is provided a method of selecting a ruminating animal having a desirable, hereditable trait comprising analyzing in the microbiome of the animal for an amount of a hereditable microorganism which is associated with the hereditable trait, wherein the amount of the hereditable microorganism is indicative as to whether the animal has a desirable hereditable trait.

According to an aspect of the present invention there is provided a method for breeding a ruminating animal comprising inseminating a female ruminating animal with semen from a male ruminating animal that has been selected according to the methods described herein, thereby breeding the ruminating animal.

According to an aspect of the present invention there is provided a method of increasing the number of ruminating animals having a desirable microbiome comprising breeding a male and female of the ruminating animals, wherein the rumen microbiome of either of the male and/or the female ruminating animals comprises a hereditable microorganism above a predetermined level, thereby increasing the number of ruminating animals having a desirable microbiome.

According to an aspect of the present invention there is provided a method of determining breed purity of ruminating animals comprising analyzing the microbiome of the ruminating animals, wherein a similarity in an amount of bacteria in the microbiome is indicative of breed purity.

According to an aspect of the present invention there is provided a method for breeding a ruminating animal comprising: inseminating a female ruminating animal that has been selected according to the methods described herein with semen from a male ruminating animal, thereby breeding the ruminating animal.

According to some embodiments of the invention, the hereditable microorganism comprises a hereditable bacteria.

According to some embodiments of the invention, the hereditable bacteria is of at least one of the operational taxonomic units (OTU) set forth in Table 1.

According to some embodiments of the invention, the hereditable bacteria is of the phylum Bacteroidetes and Firmicutes, wherein the amount is indicative as to whether the animal has a desirable hereditable trait.

According to some embodiments of the invention, the hereditable bacteria is of the order Bacteroidales and Clostridiales.

According to some embodiments of the invention, the at least one OTU is selected as set forth in any one of SEQ D NOs: 1, 3, 5, 7, 8, 9, 11-17, 19 20 or 21.

According to some embodiments of the invention, the at least one heritable bacteria is selected from the group consisting of a heritable genus of bacteria, a heritable family or bacteria and a heritable order of bacteria.

According to some embodiments of the invention, the bacteria expresses a 16S rRNA gene sequence selected from the group consisting of SEQ ID NOs: 1-22.

According to some embodiments of the invention, the at least one OTU comprises at east 5 OTUs.

According to some embodiments of the invention, the ruminating animal is a cow.

According to some embodiments of the invention, the method further comprises using the selected animal for breeding.

According to some embodiments of the invention, the desirable hereditable trait is selected from the group consisting of milk protein, dry matter intake, methane production, feed efficiency and milk fat.

According to some embodiments of the invention, the microbiome is a non-pathogenic microbiome.

According to some embodiments of the invention, the analyzing an amount is effected by analyzing the expression of at least one gene of the genome of the at least one bacteria.

According to some embodiments of the invention, the analyzing an amount is effected by sequencing the DNA derived from a sample of the microbiome.

According to some embodiments of the invention, the bacteria are of at least one of the operational taxonomic units (OTU) set forth in Table 1.

According to some embodiments of the invention, the at least one OTU is selected from the group consisting of a genus, a family and an order.

According to some embodiments of the invention, the bacteria expresses a 16S rRNA gene sequence selected from the group consisting of SEQ NOs: 1-22.

According to some embodiments of the invention, the at least one OTU comprises at least 5 OTUs.

According to some embodiments of the invention, the ruminating animal is a cow.

According to some embodiments of the invention, the microbiome comprises a rumen microbiome or a fecal microbiome.

According to some embodiments of the invention, the male ruminating animal has been selected according to the methods described herein.

According to some embodiments of the invention, the hereditable microorganism is associated with a hereditable trait.

According to some embodiments of the invention, the hereditable microorganism affects the relative amount of microbes of the microbiome.

According to some embodiments of the invention, the rumen microbiome both of the male or the female ruminating animals comprise a hereditable microorganism above a predetermined level.

According to some embodiments of the invention, the hereditable microorganism is a bacteria.

According to some embodiments of the invention, the bacteria expresses a 16S rRNA gene sequence selected from the group consisting of SEQ ID NOs: 1-22.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to a method of selecting a ruminating animal for a desired hereditable trait based on the presence of particular bacteria in the microbiome thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 8:
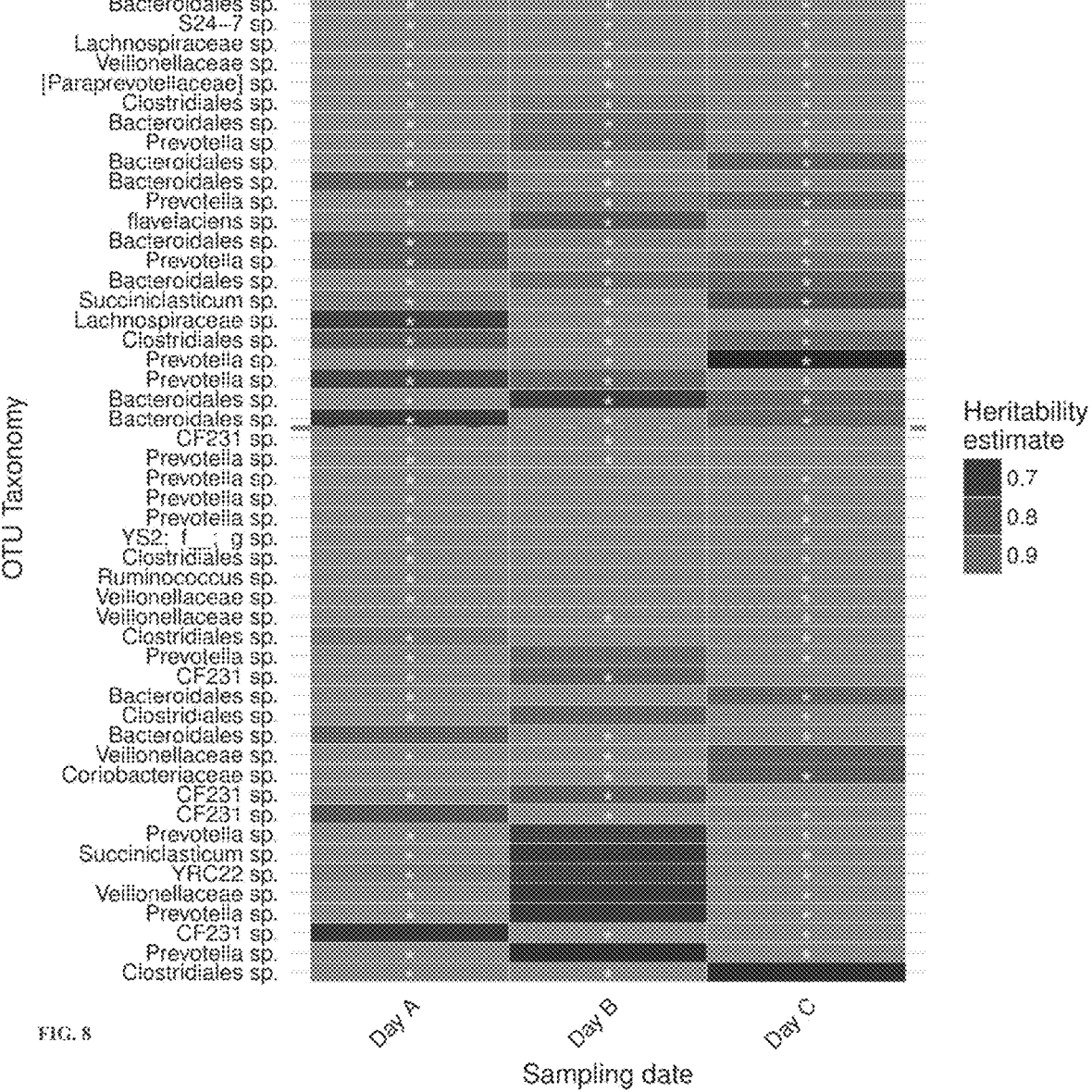
FIG. 8: 50 OTUs with top heritability estimates ordered by number of days (the microbiome was sampled in three different days) in which the heritability estimates was found significant as the primary sorting key and the mean heritability estimate as the secondary sorting key. X-Axis: sampling day. Y-Axis: microbial OTU taxonomy. Red line signifies threshold above which OTUs were considered heritable.

Ruminants sustain a long-lasting obligatory relationship with their rumen micro biome dating back 50 million years. In this unique host-microbiome relationship the host's ability to digest its feed is completely dependent on its coevolved microbiome. This extraordinary alliance raises questions regarding the dependence between ruminants' genetics and physiology and the rumen microbiome structure, composition and metabolism. To elucidate this relationship, the present inventors examined association of host genetics to phylogenetic and functional composition of the rumen microbiome. They accomplished this by studying a population of 78 milking Holstein-Friesian cows, using a combination of rumen microbiota data and other phenotypes from each animal with genotypic data from a subset of 47 animals. More specifically, by applying SNP-based heritability estimates, combined with amplicon sequencing data, host traits and rumen metabolites, the present inventors identified 22 operational taxonomic units (OTUs) whose abundances were associated with rumen metabolic traits and host physiological traits, and which showed measurable heritability (See FIG. 8).

Figure 1:
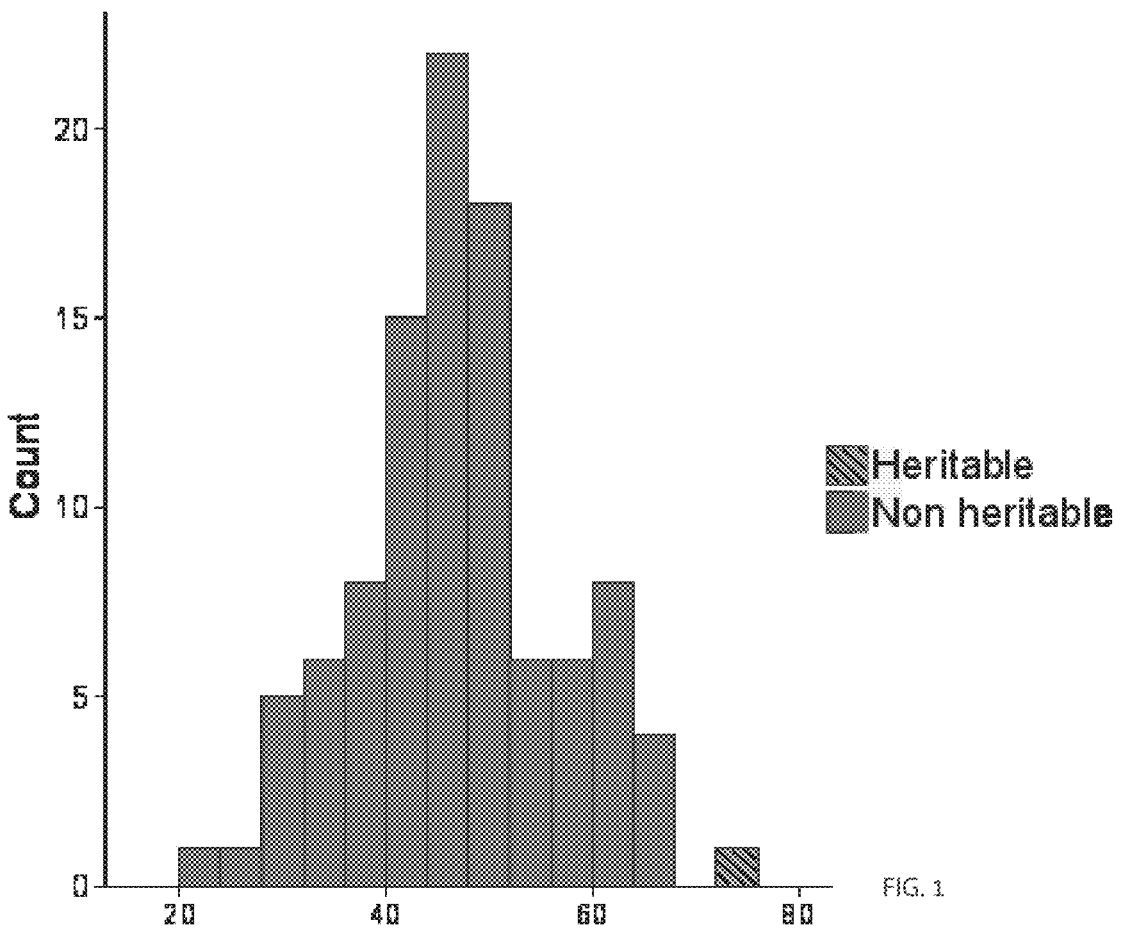
FIG. 1: The heritable portion of the bovine rumen microbiome is phylogenetically closely related. The mean pairwise similarity in the 16S rDNA gene sequence of randomly selected groups of rumen OTUs in the same size (n=22) was compared to the mean pairwise similarity of the 22 heritable OTUs. Y axis represents the number of groups and X axis represents the sequence similarity. The group of heritable OTUs with calculated mean similarity of 72% at the 16S rDNA gene sequence is depicted in pink. The distribution of randomly selected groups of rumen OTUs is depicted in blue. All random groups showed lower 16S rDNA similarity (P<0.01).

The present results show that the heritable microbial species represent a related phylogenetic group (FIG. 1). This finding corresponds with a fundamental ecological notion that organisms that share a similar ecological niche are more prone to be phylogenetically close to each other than organisms not sharing the same niche. The metabolites and physiological parameters measured are generally clustered together according to their category, based on hierarchical clustering of their correlation profile to the different heritable OTUs (columns in the heatmap, FIG. 3). For example, most amino acids cluster together, some volatile fatty acids pair together and six out of nine production indices neighbor each other along the heatmap. At the same time, from the heritable OTUs perspective, even within the distinguished niche of heritable OTUs identified in this study, one can see that the clustering of OTUs according to their abundance profiles (rows in the heatmap, FIG. 3) separates them to a high degree according to their taxonomic affiliations, e.g. eight of nine unknown family Bacteroidales cluster together and three of five *Prevotella* clustered together.

Figure 3:
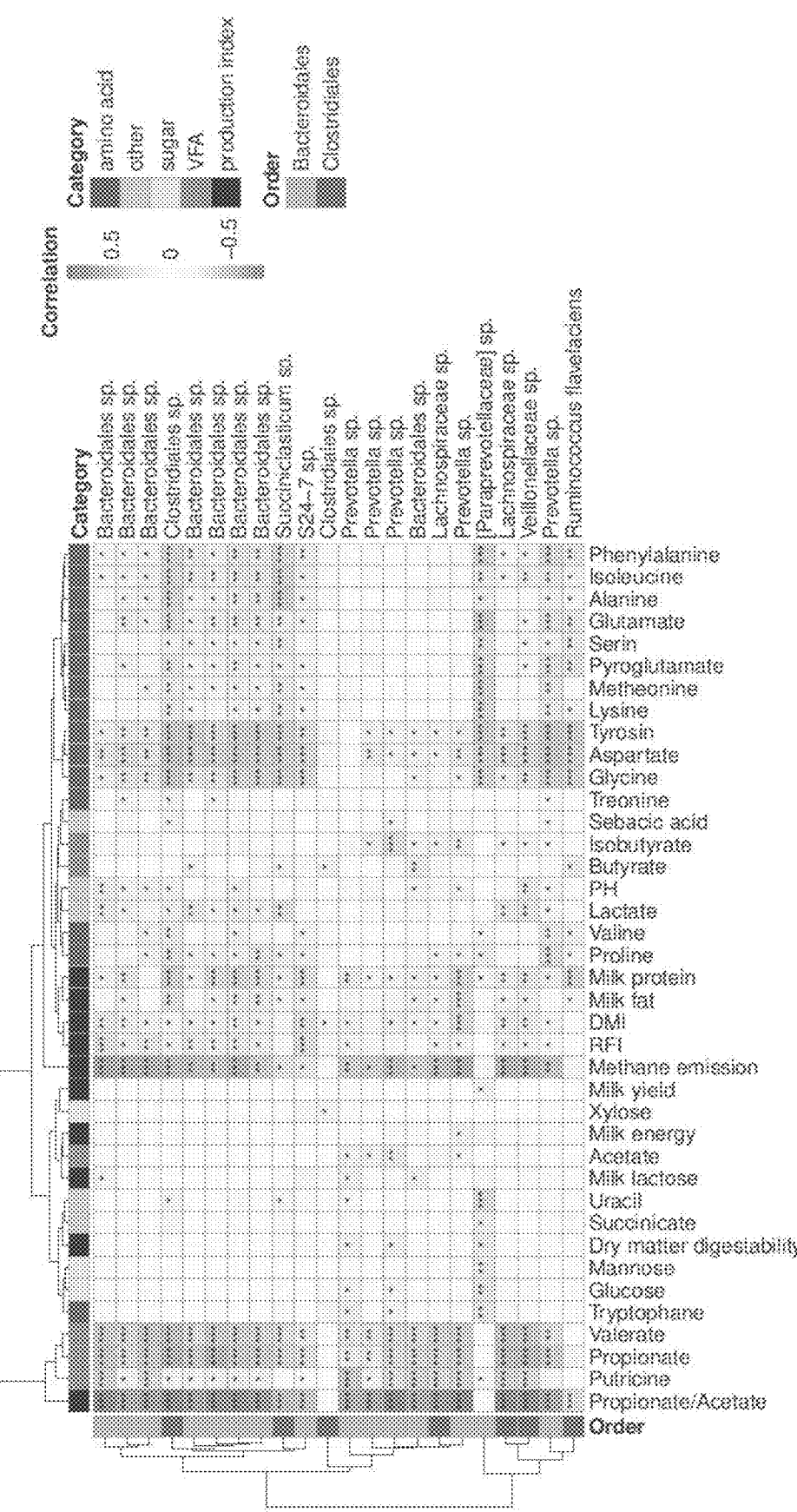
FIG. 3: Heritable OTUs are correlated to host attributes and rumen metabolites. A heatmap describing the correlation between the relative abundance of lumen heritable OTUs (rows) and selected indices representing different physiological attributes of the host or rumen metabolites (columns). OTUs are color coded by order (green represents Bacteroidales, brown represents Clostridiales). Physiological attributes are colored in black and rumen metabolites are color coded according to four groups: amino acids (blue), sugars (yellow), V FAs (green) and all other measured metabolite (grey). */*/** represent nominal p-values smaller than 0.05, 0.005 and 0.0005, respectively.
Figure 4A:
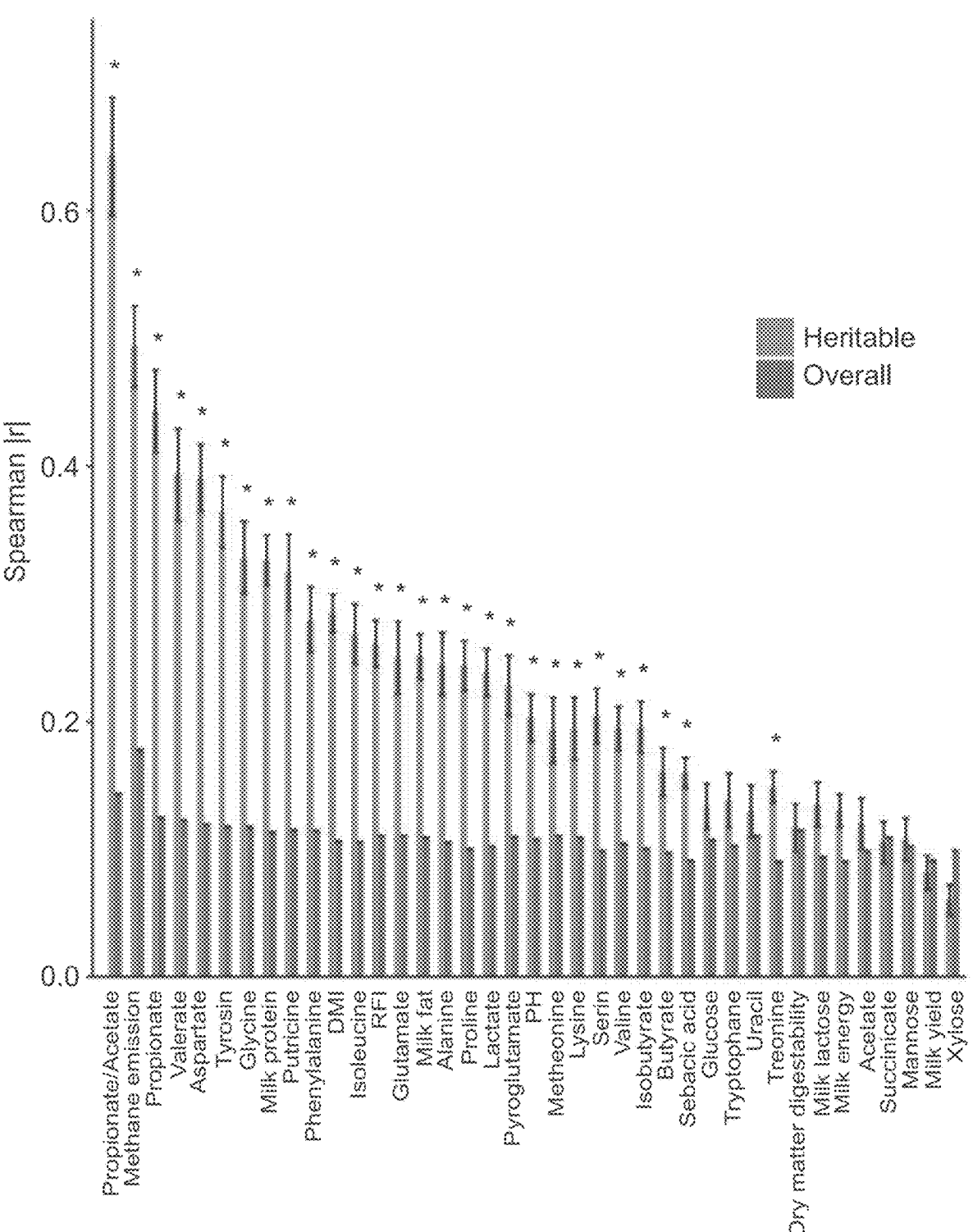
FIGS. 4A-B: Heritable OTUs are more connected to host physiology and rumen metabolites than other rumen microbes. (A) The mean absolute correlation (Spearman) of the heritable OTUs to a given index is compared with that of the entire microbiome. Asterisks represent significant difference in means (t-test, p<0.05). Red bars represent correlation of the heritable microbiome while the blue bars represent correlation of the entire microbiome. (B) The odds ratio (O. R.) of for an OTU to be correlated to a given index (nominal Spearman p<0.05), between the heritable OTUs and all OTUs. Y-Axis: odds-ratio, X-Axis: p-value derived from Fisher-exact test. Red vertical line defines the Bonferroni-corrected 0.05 significance threshold. Point colors signify category according to the legend.
Figure 4B:
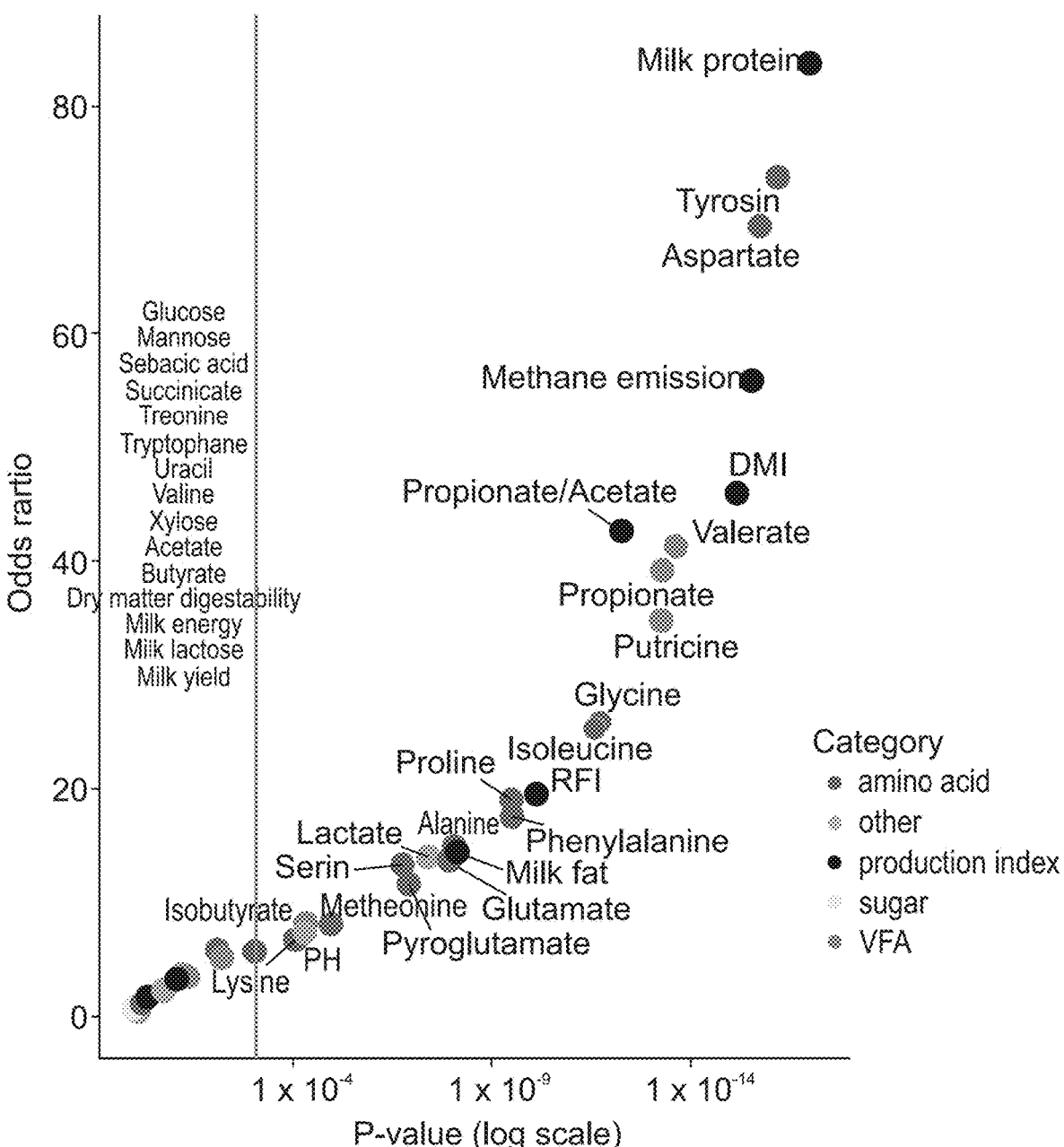

The present inventors further found that the heritable bacteria contain higher proportions of microbes correlated to host traits and to rumen metabolic parameters (FIGS. 4A and B). These findings suggest that host genetic variation can have measurable impact on physiological traits of the host as well as on rumen metabolism by potentially modulating the abundances of different groups of rumen microbes. These findings indicate that host genetics is associated with specific rumen bacteria, which are potentially more prone to influence rumen metabolism and host physiology. Notably, the metabolites and host traits that were found to be correlated to heritable bacteria were also connected by their metabolism. This could be seen in the correlation values of methane production, proionate: acetate ratio, lactate, propionate and butyrate, as well as energy harvest efficiency of the host (represented as RFI) which are correlated to the heritable bacteria. It's specifically interesting to see that the heritable bacteria are mostly correlated to the propionate: acetate ratio (mean $|r|=0.64$) which is inversely correlated to methanogenesis and lactate while positively correlated to RFI that estimates energy harvest efficiency (FIGS. 3 and 4A-B). Another noteworthy finding is the milk protein trait which was correlated to heritable microbes and exhibited the highest odds ratio, pointing to enrichment of heritable bacteria connected to this host trait (FIGS. 4A-B). These observations further strengthen the notion of a triangular relationship between the host genotype, rumen bacteria and host traits.

Thus, according to one aspect of the present invention there is provided a method of selecting a ruminating animal having a desirable, hereditable trait comprising analyzing in the microbiome of the animal for an amount of a hereditable microorganism which is associated with the hereditable trait, wherein the amount of the hereditable microorganism is indicative as to whether the animal has a desirable hereditable trait.

Ruminating animals contemplated by the present invention include for example cattle (e.g. cows), goats, sheep, giraffes, American Bison, European Bison, yaks, water buffalo, deer, camels, alpacas, llamas, wildebeest, antelope, pronghorn, and nilgai.

According to a particular embodiment, the ruminating animal is a bovine cow or bull—e.g. Bos taurus bovines or Holstein-Friesian bovines.

According to a particular embodiment, the animal which is selected is a newborn, typically not more than one day old. According to another embodiment, the animal which is selected is not more than two days old. According to another embodiment, the animal which is selected is not more than three days old. According to another embodiment, the animal which is selected is not more than 1 week old. According to another embodiment, the animal which is selected is not more than 2 weeks old. According to another embodiment, the animal which is selected is not more than 1 month old. According to another embodiment, the animal which is selected is not more than 3 months old. According to still another embodiment, the animal is an adult.

The phrase "hereditable trait" (also referred to as "heritable trait") as used herein, refers to a trait of which the variation between the individuals in a given population is due in part (or in whole) to genetic variation. Due to these genetic variations, the relative or absolute abundance of particular microbial populations in the microbiome (which serve as markers) is similar from one generation to the next generation in a statistically significant manner.

A microorganism can be classified as being hereditable when changes in its abundance amongst a group of animals can be explained by the genetic variance amongst the animals. Statistical methods which can be used in the context of the present invention include, but are not limited to Single component GRM approach, MAF-Stratified GREML (GREMLLMS), LDL and MAF-Stratified GREML (GREMLLLDMS), Single Component and MAF—Stratified LD-Adjusted Kinships (LDAK-SC and LDAK-MS), Extended Genealogy with Thresholded GRMs, Treelet Covariance Smoothing (TCS), LD-Score Regression and BOLT-REML.

In one embodiment, the trait is related to rumen metabolism, examples of which include, but are not limited to proionate:acetate ratio, amount/concentration of methane in the rumen, amount/concentration of propionic acid in the rumen and amount/concentration of valeric acid in the rumen. In addition, the trait may be the amount/concentration of an amino acid in the rumen such as Glycine, Aspartate and Tyrosin.

In another embodiment, the trait is related to a host attribute, examples of which include, but are not limited to the amount of protein or fat present in the milk of the animal, dry matter intake or feed efficiency.

Examples of hereditable traits that the present inventors have shown are at least partly hereditable include feed efficiency, methane production.

As used herein, the term "feed efficiency" refers to the ability of the animal to extract energy from its food. The feed efficiency is the difference between an animal's actual feed intake and its predicted feed intake based on its production level and body weight. Thus, an animal with "a high" feed efficiency is one that produces more milk or weighs more than what is predicted based on its feed intake. An animal with "a negative" feed efficiency is one that produces less milk or weighs less than what is predicted based on its feed intake. In one embodiment, the energy efficiency is measured using the residual feed intake (RFI) method (Koch et al., 1963, T Anim Sci, 22, 486-494) and may be calculated according to national Research Council 2001 formulas. The expected RFI values for each cow may be calculated based on a multiple regression equation.

According to one embodiment, an animal can be classified as having a low RFI (or high feed efficiency) when it has at least 0.05 standard deviations below the average RFI of the herd (with a herd being at least 15 animals).

According to one embodiment, an animal can be classified as having a low RFI (or high energy efficiency) when it has at least 0.05 standard deviations below the average RFI of the herd (with a herd being at least 15 animals).

According to one embodiment, an animal can be classified as having a low RFI (or high energy efficiency) when it has at least 1 standard deviations below the average RFI of the herd (with a herd being at least 15 animals).

According to one embodiment, an animal can be classified as having a low RFI (or high energy efficiency) when it has at least 2 standard deviations below the average RFI of the herd, with a herd being at least 15 animals.

According to one embodiment, an animal can be classified as having a low RFI (or high energy efficiency) when it has at least 3 standard deviations below the average RFI of the herd, with a herd being at least 15 animals.

According to one embodiment, an animal can be classified as having a low RFI (or high energy efficiency) when it has at least 4 standard deviations below the average RFI of the herd (with a herd being at least 15 animals).

According to one embodiment, an animal can be classified as having a low RFI (or high energy efficiency) when it has at least 5 standard deviations below the average RFI of the herd (with a herd being at least 15 animals).

According to one embodiment, an animal can be classified as having a low RFI (or high energy efficiency) when it has at least 6 standard deviations below the average RFI of the herd (with a herd being at least 15 animals).

According to one embodiment, an animal can be classified as having a high RFI (or low feed efficiency) when it has at least 0.05 standard deviations above the average RFI of the herd (with a herd being at least 15 animals).

According to one embodiment, an animal can be classified as having a high RFI (or low energy efficiency) when it has at least 0.05 standard deviations above the average RFI of the herd (with a herd being at least 15 animals).

According to one embodiment, an animal n be classified as having a high RFI (or low energy efficiency) when it has at least 1 standard deviations above the average RFI of the herd (with a herd being at least 15 animals).

According to one embodiment, an animal can be classified as having a high RFI (or low energy efficiency) when it has at least 2 standard deviations above the average RFI of the herd, with a herd being at least 15 animals.

According to one embodiment, an animal can be classified as having a high RFI (or low energy efficiency) when it has at least 3 standard deviations above the average RFI of the herd, with a herd being at least 15 animals.

According to one embodiment, an animal can be classified as having a high RFI (or low energy efficiency) when it has at least 4 standard deviations above the average RFI of the herd (with a herd being at least 15 animals).

According to one embodiment, an animal can be classified as having a high RFI (or low energy efficiency) when it has at least 5 standard deviations below the average RFI of the herd (with a herd being at least 15 animals).

According to one embodiment, an animal can be classified as having a high RFI (or low energy efficiency) when it has at least 6 standard deviations above the average RFI of the herd (with a herd being at least 15 animals).

According to one embodiment, an animal can be classified as having a low RFI (or high energy efficiency) when its dry matter intake (DMI) is less than 1 kg per day than predicted according to its expected food intake (calculated as a function of weight and milk production, as described herein above).

According to one embodiment, an animal can be classified as having a low RFI (or high energy efficiency) when its dry matter intake (DMI) is less than 2 kg per day than predicted according to its expected food intake.

According to one embodiment, an animal can be classified as having a low RFI (or high energy efficiency) when its dry matter intake (DMI) is less than 4 kg per day than predicted according to its expected food intake.

According to one embodiment, an animal can be classified as having a low RFI (or high energy efficiency) when its dry matter intake (DMI) is less than 8 kg per day than predicted according to its expected food intake.

According to one embodiment, an animal can be classified as having a low RFI (or high energy efficiency) when its dry matter intake (DMI) is less than 16 kg per day than predicted according to its expected food intake.

According to one embodiment, an animal can be classified as having a low RFI (or high energy efficiency) when its dry matter intake (DMI) is less than 32 kg per day than predicted according to its expected food intake.

According to one embodiment, an animal can be classified as having a low RFI (or high energy efficiency) when it produces 1.5 fold the amount of milk or weighs 1.5 fold the weight than predicted according to its feed intake.

According to one embodiment, an animal can be classified as having a low RFI (or high energy efficiency) when it produces 2 fold the amount of milk or weighs 2 fold the weight than predicted according to its feed intake.

According to one embodiment, an animal can be classified as having a low RFI (or high energy efficiency) when it produces 2.5 fold the amount of milk or weighs 2.5 fold the weight than predicted according to its feed intake.

According to one embodiment, an animal can be classified as having a low RFI (or high energy efficiency) when it produces 3 fold the amount of milk or weighs 3 fold the weight than predicted according to its feed intake.

According to one embodiment, an animal can be classified as having a low RFI (or high energy efficiency) when it produces 3.5 fold the amount of milk or weighs 3.5 fold the weight than predicted according to its feed intake.

According to one embodiment, an animal can be classified as having a low RFI (or high energy efficiency) when it produces 4 fold the amount of milk or weighs 4 fold the weight than predicted according to its feed intake.

According to one embodiment, an animal can be classified as having a low RFI (or high energy efficiency) when it produces 4.5 fold the amount of milk or weighs 4.5 fold the weight than predicted according to its feed intake.

According to one embodiment, an animal can be classified as having a low RFI (or high energy efficiency) when it produces 5 fold the amount of milk or weighs 5 fold the weight than predicted according to its feed intake.

The term "methane production" refers to an amount of methane emitted by the animals per se or produced by the microbiome. It may be measured in units of g per day or g per kg of dry matter intake.

According to one embodiment, an animal can be classified as "high methane producer" when it has at least 0.05 standard deviations above the average methane production of the herd.

According to one embodiment, an animal can be classified as "high methane producer" when it has at least 0.5 standard deviations above the average methane production of the herd.

According to one embodiment, an animal can be classified as "high methane producer" when it has at least 1 standard deviations above the average methane production of the herd. According to one embodiment, an animal can be classified as "high methane producer" when it has at least 2 standard deviations above the average methane production of the herd.

According to one embodiment, an animal can be classified as "high methane producer" when it has at least 3 standard deviations above the average methane production of the herd.

According to one embodiment, an animal can be classified as "high methane producer" when it has at least 4 standard deviations above the average methane production of the herd.

According to one embodiment, an animal can be classified as "high methane producer" when it has at least 5 standard deviations above the average methane production of the herd.

According to one embodiment, an animal can be classified as "high methane producer" when it has at least 6 standard deviations above the average methane production of the herd.

The term "low methane production" refers to an amount less than 100 g per day or 10 g per kg per dry matter intake produced in the microbiome (e.g. rumen microbiome/fecal microbiome) of the animal.

According to one embodiment, an animal can be classified as "low methane producer" when it has at least 0.05 standard deviations below the average methane production of the herd.

According to one embodiment, an animal can be classified as "low methane producer" when it has at least 0.5 standard deviations below the average methane production of the herd.

According to one embodiment, an animal can be classified as "low methane producer" when it has at least 1 standard deviations below the average methane production of the herd.

According to one embodiment, an animal can be classified as "low methane producer" when it has at least 2 standard deviations below the average methane production of the herd.

According to one embodiment, an animal can be classified as "low methane producer" when it has at least 3 standard deviations below the average methane production of the herd.

According to one embodiment, an animal can be classified as "low methane producer" when it has at least 4 standard deviations below the average methane production of the herd.

According to one embodiment, an animal can be classified as "low methane producer" when it has at least 5 standard deviations below the average methane production of the herd.

According to one embodiment, an animal can be classified as "low methane producer" when it has at least 6 standard deviations below the average methane production of the herd.

The term "microbiome" as used herein, refers to the totality of microbes (bacteria, fungi, protists), their genetic elements (genomes) in a defined environment.

A microbiota sample comprises a sample of microbes and or components or products thereof from a microbiome.

According to a particular embodiment, the microbiome is a rumen microbiome. In still other embodiments, the microbiome is a fecal microbiome.

According to another embodiment, the microbiome is derived from a healthy animal (i.e. the microbiome is a non-pathogenic microbiome).

In order to analyze the microbes of a microbiome, a microbiota sample is collected from the animal. This is carried out by any means that allow recovery of microbes or components or products thereof of a microbiome and is appropriate to the relevant microbiome source e.g. rumen.

Rumen may be collected using methods known in the art and include for example use of a stomach tube with a rumen vacuum sampler. Typically rumen is collected after feeding.

In some embodiments, in lieu of analyzing a rumen sample, a fecal sample is used which mirrors the microbiome of the rumen. Thus, in this embodiment, a fecal microbiome is analyzed.

According to one embodiment of this aspect of the present invention, the abundance of particular bacterial taxa are analyzed in a microbiota sample.

Methods of quantifying levels of microbes (e.g. bacteria) of various taxa are described herein below.

In some embodiments, determining a level or set of levels of one or more types of microbes or components or products thereof comprises determining a level or set of levels of one or more DNA sequences. In some embodiments, one or more DNA sequences comprise any DNA sequence that can be used to differentiate between different microbial types. In certain embodiments, one or more DNA sequences comprise 16S rRNA gene sequences. In certain embodiments, one or more DNA sequences comprise 18S rRNA gene sequences. In some embodiments, 1, 2, 3, 4, 5, 10, 15, 20, 25, 50, 100, 1,000, 5,000 or more sequences are amplified.

Taxonomy assignment of species may be performed using a suitable computer program (e.g. BLAST) against the appropriate reference database (e.g. 16S rRNA reference database).

In determining whether a nucleic acid or protein is substantially homologous or shares a certain percentage of sequence identity with a sequence of the invention, sequence similarity may be defined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BL ASTM and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed.

According to one embodiment, in order to classify a microbe as belonging to a particular genus, it must comprise at least 90% sequence homology, at least 91% sequence homology, at least 92% sequence homology, at least 93% sequence homology, at least 94 sequence homology, at least 95% sequence homology, at least 96% sequence homology, at least 97% sequence homology, at least 98 sequence homology, at least 99% sequence homology to a reference microbe known to belong to the particular genus. According to a particular embodiment, the sequence homology is at least 95%.

According to another embodiment, in order to classify a microbe as belonging to a particular species, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular species. According to a particular embodiment, the sequence homology is at least 97%.

In some embodiments, a microbiota sample is directly assayed for a level or set of levels of one or more DNA sequences. In some embodiments, DNA is isolated from a microbiota sample and isolated DNA is assayed for a level or set of levels of one or more DNA sequences. Methods of isolating microbial DNA are well known in the art. Examples include but are not limited to phenol-chloroform extraction and a wide variety of commercially available kits, including QJAamp DNA Stool Mini Kit (Qiagen, Valencia, Calif.).

In some embodiments, a level or set of levels of one or more DNA sequences is determined by amplifying DNA sequences using PCR (e.g., standard PCR, semi-quantitative, or quantitative PCR). In some embodiments, a level or set of levels of one or more DNA sequences is determined by amplifying DNA sequences using quantitative PCR. These and other basic DNA amplification procedures are well known to practitioners in the art and are described in Ausebel et al. (Ausubel F N I, Brent R, Kingston R E, Moore D, Seidman J G, Smith J A, Struhl K (eds). 1998. Current Protocols in Molecular Biology. Wiley: New York).

In some embodiments, DNA sequences are amplified using primers specific for one or more sequence that differentiate(s) individual microbial types from other, different microbial types. In some embodiments, 16S rRNA gene sequences or fragments thereof are amplified using primers specific for 16S rRNA gene sequences. In some embodiments, 18S DNA sequences are amplified using primers specific for 18S DNA sequences.

In some embodiments, a level or set of levels of one or more 16S rRNA gene sequences is determined using phylochip technology. Use of phylochips is well known in the art and is described in Hazen et al. ("Deep-sea oil plume enriches indigenous oil-degrading bacteria." Science, 330, 204-208, 2010), the entirety of which is incorporated by reference. Briefly, 16S rRNA genes sequences are amplified and labeled from DNA extracted from a microbiota sample. Amplified DNA is then hybridized to an array containing probes for microbial 16S rRNA genes. Level of binding to each probe is then quantified providing a sample level of microbial type corresponding to 16S rRNA gene sequence probed. In some embodiments, phylochip analysis is performed by a commercial vendor. Examples include but are not limited to Second Genome Inc. (San Francisco, Calif.).

In some embodiments, determining a level or set of levels of one or more types of microbes or components or products thereof comprises determining a level or set of levels of one or more microbial RNA molecules (e.g., transcripts). Methods of quantifying levels of RNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York).

In some embodiments, determining a level or set of levels of one or more types of microbes or components or products thereof comprises determining a level or set of levels of one or more microbial proteins. Methods of quantifying protein levels are well known in the art and include but are not limited to western analysis and mass spectrometry. These and all other basic protein detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York). In some embodiments, determining a level or set of levels of one or more types of microbes or components or products thereof comprises determining a level or set of levels of one or more microbial metabolites. In some embodiments, levels of metabolites are determined by mass spectrometry. In some embodiments, levels of metabolites are determined by nuclear magnetic resonance spectroscopy. In some embodiments, levels of metabolites are determined by enzyme-linked immunosorbent assay (ELISA). In some embodiments, levels of metabolites are determined by colorimetry. In some embodiments, levels of metabolites are determined by spectrophotometry.

In some embodiments, what is determined is the distribution of microbial families within the microbiome. However, characterization may be carried to more detailed levels, e.g. to the level of genus and/or species, and/or to the level of strain or variation (e.g. variants) within a species, if desired (including the presence or absence of various genetic elements such as genes, the presence or absence of plasmids, etc.). Alternatively, higher taxanomic designations can be used such as Phyla, Class, or Order. The objective is to identify which microbes (usually bacteria, but also optionally fungi (e.g. yeasts), protists, etc.) are present in the sample from the ruminating animal and the relative distributions of those microbes, e.g. expressed as a percentage of the total number of microbes that are present, thereby establishing a micro floral pattern or signature for the animal being tested.

In other embodiments of the invention, when many taxa are being considered, the overall pattern of microflora is assessed, i.e. not only are particular taxa identified, but the percentage of each constituent taxon is taken in account, in comparison to all taxa that are detected and, usually, or optionally, to each other. Those of skill in the art will recognize that many possible ways of expressing or compiling such data exist, all of which are encompassed by the present invention. For example, a "pie chart" format may be used to depict a microfloral signature; or the relationships may be expressed numerically or graphically as ratios or percentages of all taxa detected, etc. Further, the data may be manipulated so that only selected subsets of the taxa are considered (e.g. key indicators with strong positive correlations). Data may be expressed, e.g. as a percentage of the total number of microbes detected, or as a weight percentage, etc.

Methods of analyzing the similarity of the genetic background of two ruminating animals may be carried out using genotyping assays known in the art.

As used herein, the term "genotyping" refers to the process of determining genetic variations among individuals in a species. Single nucleotide polymorphisms (SNPs) are the most common type of genetic variation that are used for genotyping and by definition are single-base differences at a specific locus that is found in more than 1% of the population. SNPs are found in both coding and non-coding regions of the genome and can be associated with a phenotypic trait of interest such as a quantitative phenotypic trait of interest. Hence, SNPs can be used as markers for quantitative phenotypic traits of interest. Another common type of genetic variation that are used for genotyping are "InDels" or insertions and deletions of nucleotides of varying length. For both SNP and InDel genotyping, many methods exist to determine genotype among individuals. The chosen method generally depends on the throughput needed, which is a function of both the number of individuals being genotyped and the number of genotypes being tested for each individual. The chosen method also depends on the amount of sample material available from each individual or sample. For example, sequencing may be used for determining presence or absence of markers such as SNPs, e.g. such as Sanger sequencing and High Throughput Sequencing technologies (HTS). Sanger sequencing may involve sequencing via detection through (capillary) electrophoresis, in which up to 384 capillaries may be sequence analysed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT). HTS technologies are available such as offered by Roche, Illumina and Applied Biosystems (Life Technologies) Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies have their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

Low density and high density chips are contemplated for use with the invention, including SNP arrays comprising from 3,000 to 800,000 SNPs. By way of example, a "50K" SNP chip measures approximately 50,000 SNPs and is commonly used in the livestock industry to establish genetic merit or genomic estimated breeding values (GEBVs). In certain embodiments of the invention, any of the following SNP chips may be used: BovineSNP50 v1 BeadChip (Illumina), Bovine SNP v2 BeadChip (Illumina), Bovine 3K BeadChip (Illumina), Bovine LD BeadChip (Illumina), Bovine HD BeadChip Geneseek® Genomic Profiler® BeadChip, or Geneseek® Genomic Profiler™ HD BeadChip.

In one embodiment, in order to measure the genetic similarity between the animals the genetic relatedness between the animals based on the SNP data is calculated. To this end a matrix that estimates the genetic relatedness between each unique pair of animals can be produced. This matrix is based on the count of shared alleles, weighted by the allele's rareness:

$$A_{jk} = \frac{1}{n} \Sigma_{i=1}^{n} \left( \frac{(x_{ij} - 2p_i)(x_{ik} - 2p_i)}{2p_i(1 - p_i)} \right)$$

where Ajk represents the genetic relationship estimate between animals j and k; xij and xik are the counts of the reference alleles in animals j and k, respectively; pi is the proportion of the reference allele in the population; and n is the total number of SNPs used for the relatedness estimation.

In order to identify microbial species where significant proportions of their variation in abundance profiles can be attributed to heritable genetic factors, the microbiota sample is analyzed so as to uncover taxa (e.g. species) of microbes showing similar abundance (either absolute or relative) in animals that share a similar genetic background.

In one embodiment, microbes or OTUs that exhibits a significant heritable component are considered as such if their heritability estimate is of >0.01 and P value of <0.1. It will be appreciated that the confidence level may be increased or decreased according to the stringency of the test. Thus, for example in another embodiment, microbes that exhibits a significant heritable component are considered as such if their heritability estimate is of >0.01 and P value of <0.05. Other contemplated heritability estimates contemplated by the present inventors include >0.02 and P value of <0.1, >0.03 and P value of <0.1, >0.04 and P value of <0.1, >0.05 and P value of <0.1, >0.06 and P value of <0.1, >0.07 and P value of <0.1, >0.08 and P value of <0.1, >0.09 and P value of <0.1, >0.1 and P value of <0.1, >0.2 and P value of <0.1, >0.3 and P value of <0.1, >0.4 and P value of <0.1, >0.5 and P value of <0.1, >0.6 and P value of <0.1, >0.7 and P value of <0.1, >0.8 and P value of <0.1.

Other contemplated heritability estimates contemplated by the present inventors include >0.02 and P value of <0.05, >0.03 and P value of <0.05, >0.04 and P value of <0.05, >0.05 and P value of <0.05, >0.06 and P value of <0.05, >0.07 and P value of <0.05, >0.08 and P value of <0.05, >0.09 and P value of 0.05, >0.1 and P value of 0.05, >0.2 and P value of 0.05, >0.3 and P value of 0.05, >0.4 and P value of 0.05, >0.5 and P value of 0.05, >0.6 and P value of 0.05, >0.7 and P value of 0.05, >0.8 and P value of 0.05.

According to a particular embodiment, the heritability estimate is >0.7 and a P value of <0.05.

To increase the confidence of the analysis, the heritability analysis may be limited exclusively to bacterial taxa which are present in at least 20%, 25%, 30%, 40%, 50% or higher of the genotyped subset. In addition, heritability analyses for each bacterial taxa may be performed a number of times, e.g. on a number of different sampling days (e.g. 2, 3, 4, 5, or more days). Only bacterial taxa that exhibited a significant heritable component (e.g. heritability estimate of >0.7 and p-value <0.05) in all individual sampling days, could be considered as heritable.

In one embodiment, the heritable bacteria belong to the phylum Bacteroidetes and/or Firmicutes, wherein the amount of the phylum is indicative as to whether the animal has a desirable hereditable trait.

In another embodiment, the hereditable bacteria belong to the order Bacteroidales and/or Clostridiales, wherein the amount of the phylum is indicative as to whether the animal has a desirable hereditable trait.

As mentioned, whilst carrying out the procedures described herein above, the present inventors identified 22 OTUs that match the criteria of being heritable.

The term "OTU" as used herein, refers to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share greater than 97% average nucleotide identity across the entire 16S or some variable region of the 16S are considered the same OTU. See e.g., Claesson et al., 2010. Comparison of two next-generation sequencing technologies for resolving highly complex microbiota composition using tandem variable 16S rRNA gene regions. Nucleic Acids Res 38: e200. Konstantinidis et al., 2006. The bacterial species definition in the genomic era. Philos Trans R Soc Lond B Biol Sci 361: 1929-1940. In embodiments involving the complete genome, MLSTs, specific genes, other than 16S, or sets of genes OTUs that share, greater than 95% average nucleotide identity are considered the same OTU. See e.g., Achtman and Wagner. 2008. Microbial diversity and the genetic nature of microbial species. Nat. Rev. Microbial. 6: 431-440; Konstantinidis et al., 2006, supra. The bacterial species definition in the genomic era. Philos Trans R Soc Lond B Biol Sci 361: 1929-1940. OTUs can be defined by comparing sequences between organisms. Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Such characterization employs, e.g., WGS data or a whole genome sequence. As used herein, a "type" of bacterium refers to an OTU that can be at the level of a strain, species, clade, or family.

In one embodiment, the OTU is set forth in Table 1 herein below.

TABLE 1

```
>denovo103806 k_Bacteria; p_Bacteroidetes: c_Bacteroidia; o_Bacteroidales;
SEQ ID NO: 1
TGAGGAATATTGGTCAATGGACGGAAGTCTGAACCAGCCATGCCGCGTGAAGGAAGAA
TGCCCTATGGGTTGTAAACTTGTTTTGCCGCAGAGTAATAAGGGGCGTGCGCGCCCCGA
TGAGAGTATGCGGCGAATAAGCATCGGCTAACTCCGTGCCAGCAGCCGCGGTAATACG
GAGGATGCGAGCGTTATCCGGATtTATTGGGTTTAAAGGGTGCGCAGGCGGACAGCTA
AGTCAGCGGTGAAATAT >denovo113091 k_Bacteria: p_Bacteroidetes: c_Bacteroidia; o_Bacteroidales;
SEQ ID NO: 2
TGAGGAATATTGGACAATGGCCGAGAGGCTGATCCAGCCATGCCGCGTGCGGGAAGAC
GGCCCTATGGGTTGTAAACCGCTTTTGTCGGGGAGCAATAAGGTCCACGCGTGGACTGA
TGAGAGTACCTGGCGAATAAGCATCGGCTAACTCCGTGCCAGCAGCCGCGGTAATACG
GAGGATGCAAGCGTTATCCGGATTTATTGGGTTTAAAGGGTGCGTAGGCGGCGAGGTA
AGCGTGAGGTGAAAGCT
```

TABLE 1 -continued

```
>denovo21902 k_Bacteria; p_Firmicutes; c_Clostridia; o_Clostridiales;
SEQ ID NO: 3
TGGGGAATATTGGGCAATGGGGGGAACCCTGACCCAGCAACGCCGCGTGGAGGAAGA
AGGTCTTCGGATCGTAAACTCCTGTCCTAAGAGACGAGCAGGAGACGGTAACTTAGGA
GGAAGCCCCGGCTAACTACGTGCCAGCAGCCGCGGTAATACGTAGGGGGCAAGCGTTG
TCCGGAATGATTGGGCGTAAAGGGCGCGTAGGCGGCCGCAGAAGTCTGAAGTGAAATA
CCCGCTTTCAAGGTGGGTA >denovo246439 k_Bacteria: p_Bacteroidetes; c_Bacteroidia; o_Bacteroidales;
SEQ ID NO: 4
TGAGGAATATTGGTCAATGGGCGGAAGCCTGAACCAGCCATGCCGCGTGTGGGAAGAA
GGCCCTATGGGTTGTAAACCACTTTTAGCCGGGAGTAATAAGGGGCGTGCGCGCCCCG
ATGAGAGTACCGGCGGAATAAGCATCGGCTAACTCCGTGCCAGCAGCCGCGGTAATAC
GGAGGATGCAAGCGTTATCCGGATTTATTGGGTTTAAAGGGTGCGTAGGCGGACCGTT
AAGTCAGCGGTGAAAGGT >denovo311676 k_Bacteria; p_Bacteroidetes; c_Bacteroidia; o_Bacteroidales:
SEQ ID NO: 5
TGAGGAATATTGGTCAATGGACGGAAGTCTGAACCAGCCATGCCGCGTGCGGGAAGAC
GGCCCTATGGGTTGTAAACCGCTTTTCCCCGGGAGTAATAAGGCCCGTGCGCGGGCCGA
TGAGAGTACCGGGGGAATAAGCATCGGCTAACTCCGTGCCAGCAGCCGCGGTAATACG
GAGGATGCAAGCGTTATCCGGATTTATTGGGTTTAAAGGGTGCGTAGGCGGACCGTTA
AGTCAGCGGTGAAATGT >denovo443895 k__Bacteria: p_Firmicutes; c_Clostridia; o_Clostridiales:
SEQ ID NO: 6
TGGGGAATATTGGGCAATGGGCGAAAGCCTGACCCAGCAACGCCGCGTGAGTGAAGAA
GGCCTTCGGGTTGTAAAGCTCTGTTATAGTTGACGAAGGAAGTGACGGTAGGCTATAA
GGAAGCCCCGGCTAACTACGTGCCAGCAGCCGCGGTAATACGTAGGGGGCGAGCGTTG
TCCGGAATGACTGGGCGTAAAGGGCGTGTAGGCGGTCATTTAAGTCTGGAGTGAAAGT
CCTGCATTCAATGTGGGA >denovo462168 k_Bacteria; p_Firmicutes; c_Clostridia; o_Clostridiales;
f_Veillonellaceae; g_Succiniclasticum; SEQ ID NO: 7
TGGGGAATCTTCCGCAATGGGCGCAAGCCTGACGGAGCAACGCCGCGTGGGTGAGGAA
GTTCTTCGGAACGTAAAGCCCTGTTGTACATGACGAACGTGTATCCTATCAACAACGGG
ATGCAATGACGGTAGTGTACGAGGAAGCCACGGCTAACTACGTGCCAGCAGCCGCGGT
AATACGTAGGTGGCAAGCGTTGTCCGGAATTATTGGGCGTAAAGCGCATGTAGGCGGT
GATGTAAGTCTGTCGTG >denovo467472 k_Bacteria; p_Bacteroidetes; c_Bacteroidia; o_Bacteroidales;
SEQ ID NO: 8
TGAGGAATATTGGACAATGGCCGAGAGGCTGATCCAGCCATGCCGCGTGCGGGAAGAC
GGCCCTATGGGTTGTAAACCGCTTTTGTTGGGAGAGCAATAAGAGTCACGTGTGACTTGA
TGAGAGTATCCAGCGAATAAGCATCGGCTAACTCCGTGCCAGCAGCCGCGGTAATACG
GAGGATGCGAGCGTTATCCGGATTTATTGGGTTTAAAGGGTGCGTAGGCGGATGATTA
AGCGTGAGGTGAAATGC >denovo475173 k_Bacteria; p_Bacteroidetes; c_Bacteroidia; o_Bacteroidales;
f_Prevotellaceae; g_Prevotella; SEQ ID NO: 9
TGAGGAATATTGGTCAATGGGCGAGAGCCTGAACCAGCCAAGTAGCGTGCAGGATGAC
GGCCCTATGGGTTGTAAACTGTTTTGCATGGGAATAAAGTGCGGGACGCGTCCCGTTT
TGTATGTACCATGAGAATAAGGACCGGCTAATTCCGTGCCAGCAGCCGCGGTAATACG
GAAGGTCCGGGCGTTATCCGGATTTATTGGGTTTAAAGGGAGCGCAGGCTGGAGATTA
AGCGTGACGTGAAATGC >denovo582030 k_Bacteria; p_Bacteroidetes; c_Bacteroidia; o_Bacteroidales;
SEQ ID NO: 10
TGAGGAATATTGGTCAATGGGCGGAAGCCTGAACCAGCCAAGTCGCGTGAAGGATGAA
GGCATTATGTGTTGTAAACTTCTTTAGCTGTGGAGAAATAAGGTGGTCGAGACCACCGA
TGCTAGTACACAGAGAATAAGGATCGGCTAACTCCGTGCCAGCAGCCGCGGTAATACG
GAGGATCCGAGCGTTATCCGGATTCATTGGGTTTAAAGGGTGCGCAGGCGGTGCCTTAA
GTCAGCGGTAAAATCG >denovo610253 k_Bacteria: p_Bacteroidetes; c_Bacteroidia; o_Bacteroidales;
f_S24-7; SEQ ID NO: 11
TGAGGAATATTGGTCAATGGGCGGTAGCCTGAACCAGCCAAGTCGCGTGCGGGAAGAA
GGCCCTACGGGTCGTAAACCGCTTTTGTCGGGGAGCAAAGTGCGCCACGTGTGGTGTAT
TGCGAGTACCCGAAGAAAAAGCATCGGCTAACTCCGTGCCAGCAGCCGCGGTAATACG
GAGGATGCGAGCGTTATCCGGATTTATTGGGTTTAAAGGGTGCGCAGGCGGCGCGTCA
AGTCAGCGGTGAAAATG >denovo65476 k_Bacteria: p_Bacteroidetes; c_Bacteroidia: o_Bacteroidales;
f_Prevotellaceae; g_Prevotella; SEQ ID NO: 12
TTCGGCATATTGGTCAATGGGCGCGAGCCTGAACCAGCCAAGTAGCGTGCAGGATGAC
GGCCCTATGGGTTGTAAACTGCTTTTATATAGGGATAAAGTCGGGGACGTGTCCCCGTT
TGTAGGTACTATATGAATAAGGACCGGCTAATTCCGTGCCAGCAGCCGCGGTAATACG
GAAGGTCCGGGCGTTATCCGGATTTATTGGGTTTAAAGGGAGCGCAGGCCGGAGGCTA
AGCGTGACGTGAAATGT
```

TABLE 1 -continued

```
>denovo67695 k_Bacteria; p_Bacteroidetes; c_Bacteroidia; o_Bacteroidales;
SEQ ID NO: 13
TGAGGAATATTGGACAATGGCCGAAAGGCTGATCCAGCCATGCCGCGTGCGGGAAGAC
GGCCCTATGGGTTGTAAACCGCTTTTGTTGGGGAGCAATAAGGGCCACGTGTGACCCGA
TGAGAGTACCCAGCGAATAAGCATCGGCTAACTCCGTGCCAGCAGCCGCGGTAATACG
GAGGATGCAAGCGTTATCCGGATTTATTGGGTTTAAAGGGTGCGTAGGCGGACGATTA
AGCGTGAGGTGAAATGC >denovo698975 k_Bacteria; p_Bacteroidetes; c_Bacteroidia; o_Bacteroidales;
f_[Paraprevotellaceae]; SEQ ID NO: 14
TGAGGAATATTGGTCAATGGGCGGAAGCCTGAACCAGCCAAGTAGCGTGAAGGATGAC
GGCCCTACGGGTTGTAAACTTCTTTTATGCGGGAACAAAGTGCGCCACGCGTGGCGTTT
TGCGCGTACCGCAGGAAAAAGCACCGGCTAATTCCGTGCCAGCAGCCGCGGTAATACG
GAAGGTGCGAGCGTTATCCGGATTCATTGGGTTTAAAGGGAGCGTAGGCGGAGCGCCA
AGTCAGCTGTGAAATCC >denovo746686 k_Bacteria; p_Firmicutes; c_Clostridia; o_Clostridiales;
f_Lachnospiraceae; SEQ ID NO: 15
TGGGGAATATTGCACAATGGAGGAAACTCTGATGCAGCGACGCCGCGTGAGTGAAGAA
GTATTTCGGTATGTAAAGCTCTATCAGCAGGGAAGATAATGACGGTACCTGAATAAGA
AGCACCGGCTAAATACGTGCCAGCAGCCGCGGTAATACGTATGGTGCAAGCGTTATCC
GGATTTACTGGGTGTAAAGGGAGTGCAGGCGGTCTGAAAAGTCAGATGTGAAAGCCCG
GGGCTCAACCCCGGGACT >denovo780334 k_Bacteria; p_Firmicutes; c_Clostridia; o_Clostridiales;
f_Lachnospiraceae; SEQ ID NO: 16
TGGGGAATATTGCACAATGGGGGAAACCCTGATGCAGCGACGCCGCGTGAGTGAAGAA
GTATTTCGGTATGTAAAGCTCTATCAGCAGGGAAGAAAATGACGGTACCTGACTAAGA
AGCCCCGGCTAACTACGTGCCAGCAGCCGCGGTAATACGTAGGGGGGCAAGCGTTATCC
GGATTTACTGGGTGTAAAGGGAGCGCAGACGGAAGAACAAGTCTGATGTGAAATGCGG
GGGCTCAACTCCTGAATT >denovo780566 k_Bacteria; p_Bacteroidetes; c_Bacteroidia; o_Bacteroidales;
f_Prevotellaceae; g_Prevotella; SEQ ID NO: 17
TGAGGAATATTGGTCAATGGGCGAGAGCCTGAACCAGCCAAGTAGCGTGCAGGAAGAC
GGCCCTATGGGTTGTAAACTGCTTTTATATAGGGATAAAGTCGGGGACGTGTCCCCGTT
TGTAGGTACTATATGAATAAGGACCGGCTAATTCCGTGCCAGCAGCCGCGGTAATACG
GAAGGTCCGGGCGTTATCCGGATTTATTGGGTTTAAAGGGAGCGCAGGCCGGCTTTTAA
GCGTGACGTGAAATGT >denovo794443 k_Bacteria; p_Bacteroidetes; c_Bacteroidia; o_Bacteroidales;
f_Prevotellaceae; g_Prevotella; SEQ ID NO: 18
TGAGGAATATTGGTCAATGGGCGCGAGCCTGAACCAGCCAAGTAGCGTGCAGGATGAC
GGCCCTATGGGTTGTAAACTGCTTTTGGAGGGGAATAAAGTCGTCTACGTGTAGGTGTT
TGCATGTACCCTCAGAATAAGGACCGGCTAATTCCGTGCCAGCAGCCGCGGTAATACG
GAAGGTCCTGGCGTTATCCGGATTTATTGGGTTTAAAGGGAGCGCAGGCGGGCGATTA
AGCGTGACGTGAAATGC >denovo812512 k_Bacteria; p_Bacteroidetes; c_Bacteroidia; o_Bacteroidales;
f_Prevotellaceae; g_Prevotella; SEQ ID NO: 19
TGAGGAATATTGGTCAATGGCCGCGAGGCTGAACCAGCCAAGTAGCGTGCAGGATGAC
GGCCCTCTGGGTTGTAAACTGCTTTTATGCGGGAACAAAGGCGTCTACGTGTAGTCGTG
TGCGTACCGCAGGAAAAAGGACCGGCTAATTCCGTGCCAGCAGCCGCGGTAATACG
GAAGGTCCGGGCGTTATCCGGATTTATTGGGTTTAAAGGGAGCGCAGGCTGAAGCGCA
AGCCGGCTGTAAAATTT >denovo836347 k_Bacteria; p_Bacteroidetes; c_Bacteroidia; o_Bacteroidales;
SEQ ID NO: 20
TGAGGAATATTGGTCAATGGGCGGAAGCCTGAACCAGCCAAGTCGCGTGAAGGATGAA
GGTATTATGTATTGTAAACTTCTTTAGCTGTGGAGAAATAAGGTGCTCGTGAGCACCGA
TGCTAGTACACAGAGAATAAGGGTCGGCTAACTCCGTGCCAGCAGCCGCGGTAATACG
GAGGACCCGAGCGTTATCCGGATTCATTGGGTTTAAAGGGTGCGCAGGCGGCTTCTTAA
GTCAGCGGTAAAATCG >denovo875125 k_Bacteria; p_Firmicutes; c_Clostridia; o_Clostridiales;
f_Ruminococcaceae; g_Ruminococcus; s_flavefaciens SEQ ID NO: 21
TGGGGAATCTTCCGCAATGGGGGAAAGCCTGACGGAGCAACGCCGCGTGAGTGAAGAA
GGTCTTCGGATCGTAAAGCTCTGTTGAAGGGGACGCACGGCGCCTGTTACAAGATAGC
AGGTGAATGACGGTACCCTTCGAGGAAGCCACGGCTAACTACGTGCCAGCAGCCGCGG
TAATACGTAGGCGGCAAGCGTTGTCCGGAATCATTGGGCGTAAAGGGAGCGCAGGTGG
ACGTATAGGTCCTTCTTA >denovo887467 k_Bacteria; p_Firmicutes; c_Clostridia; o_Clostridiales;
f_Ruminococcaceae; g_Ruminococcus; s_flavefaciens SEQ ID NO: 22
TGGGGAATATTGCACAATGGGGGAAACCCTGATGCAGCGATGCCGCGTGGAGGAAGAA
GGTTTTCGGATTGTAAACTCCTGTCTTAAAGGACGATAATGACGGTACTTTAGGAGGAA
GCTCCGGCTAACTACGTGCCAGCAGCCGCGGTAATACGTAGGGAGCGAGCGTTGTCCG
```

TABLE 1 -continued

GAATTACTGGGTGTAAAGGGAGCGTAGGCGGGAGTGCAAGTCAGATGTGAAATACATG
GGCTCAACCCATGGGCT

In one embodiment, the OTU is set forth in any one of the sequences set forth in SEQ ID NOs: 1-22. In another embodiment, the OTU is set forth in SEQ ID NOs: 1, 3, 5, 7, 8, 9, 11-17, 19, 20 or 21.

Specific OTUs for specific traits are summarized in Table 2, herein below. In the table, (1) signifies a positive correlation, (−1) signifies a negative correlation and (0) signifies so significant correlation.

according to the methods of any one of claims of the current invention, thereby breeding the ruminating animal.

The breeding of the one or more bovine bulls with the bovine cows is preferably by artificial insemination, but may alternatively be by natural insemination.

According to still another aspect of the present invention there is provided a method determining breed purity of ruminating animals comprising analyzing the microbiome of

TABLE 2

| SEQ ID NO: | aspartate | glycine | Tyrosine | Propionic acid | valeric. acid | Propionate/ acetate | DMI_ Normalized | Methane emission | milk_fat | milk_protein | RFI_Total |
|---|---|---|---|---|---|---|---|---|---|---|---|
| 3 | 0 | 0 | 0 | 0 | 0 | 0 | 1 | 0 | 0 | 0 | 0 |
| 12 | 1 | 0 | 1 | −1 | −1 | −1 | 0 | 1 | 0 | 1 | 0 |
| 13 | 1 | 1 | 1 | −1 | −1 | −1 | 1 | 1 | 1 | 1 | 1 |
| 1 | 1 | 1 | 1 | −1 | −1 | −1 | 1 | 1 | 0 | 1 | 1 |
| 2 | 1 | 1 | 1 | −1 | −1 | −1 | 1 | 1 | 1 | 1 | 1 |
| 4 | 1 | 1 | 1 | −1 | −1 | −1 | 1 | 1 | 1 | 1 | 1 |
| 5 | 1 | 1 | 1 | −1 | −1 | −1 | 1 | 1 | 1 | 1 | 1 |
| 6 | 1 | 1 | 1 | −1 | −1 | −1 | 1 | 1 | 1 | 1 | 1 |
| 7 | 1 | 1 | 1 | −1 | −1 | −1 | 0 | 1 | 1 | 1 | 0 |
| 8 | 1 | 1 | 1 | −1 | −1 | −1 | 1 | 1 | 1 | 1 | 0 |
| 9 | 0 | 0 | 0 | −1 | −1 | −1 | 1 | 1 | 0 | 1 | 1 |
| 10 | 1 | 1 | 1 | −1 | −1 | −1 | 1 | 1 | 0 | 1 | 1 |
| 11 | 1 | 1 | 1 | −1 | −1 | −1 | 1 | 1 | 1 | 1 | 1 |
| 14 | −1 | −1 | −1 | 0 | 0 | 0 | 0 | 0 | 0 | −1 | 0 |
| 15 | −1 | −1 | −1 | 1 | 1 | 1 | −1 | −1 | −1 | −1 | −1 |
| 16 | 1 | 0 | 1 | −1 | −1 | −1 | 1 | 1 | 1 | 1 | 1 |
| 17 | 1 | 0 | 1 | −1 | −1 | −1 | 1 | 1 | 0 | 1 | 0 |
| 18 | 1 | 1 | 1 | −1 | −1 | −1 | 1 | 1 | 1 | 1 | 1 |
| 19 | −1 | −1 | −1 | 1 | 1 | 1 | −1 | −1 | 0 | −1 | −1 |
| 20 | 1 | 1 | 1 | −1 | −1 | −1 | 1 | 1 | 0 | 0 | 1 |
| 21 | −1 | −1 | −1 | 1 | 1 | 1 | −1 | −1 | −1 | −1 | −1 |
| 22 | −1 | −1 | −1 | 0 | 0 | 1 | 0 | 0 | −1 | −1 | 0 |

The present invention further contemplates analysing a plurality of the above described OTUs. Thus, at least one OTU, at least two, at least three, at least four, at least five, at least six, at least seven, at least eight, at least nine, at least ten, at least U, at least 12, at least 13, at least 14, at least 15 or all of the above described OTUs are analysed.

It will be appreciated that once the animal has been classified as having sufficient quantity of a heritable microorganism that correlates with a desirable phenotype, it may be selected (e.g. separated from the rest of the herd) and classified as having that phenotype. According to one embodiment, the animal branded such that it is clear that it comprises this phenotype.

In one embodiment, the animal is selected as being a candidate for breeding. Thus, the animal may be deemed suitable as a gamete donor for natural mating, artificial insemination or in vitro fertilization.

Thus, according to another aspect of the present invention there is provided a method for breeding a ruminating animal comprising: inseminating a female ruminating animal that has been selected according to the methods described herein with semen from a male ruminating animal, thereby breeding the ruminating animal.

According to another aspect of the present invention there is provided a method for breeding a ruminating animal comprising: inseminating a female ruminating animal with semen from a male ruminating animal that has been selected the ruminating animals, wherein a similarity in an amount of bacteria in the microbiome is indicative of breed purity.

Thus, two animals of the same species may be deemed to be of the same breed, when the quantity (e.g. occurrence) in the microbiome of at least one, at least two, at least three, at least four, at least five, at least six, at least seven, at least eight, at least nine, or even at least 10 or all of the bacterial OTUs set forth in Table 1 is statistically significantly similar. According to another embodiment, two animals of the same species may be deemed to be of the same breed, when the quantity (e.g. the relative ratio) in the microbiome of at least 10%, 20%, 30%, 40%, 50%, 60% or even 70% of the bacteria belonging to phylum Bacteroidetes and/or Firmicutes, or belonging to the order Bacteroidales and/or Clostridiales are identical.

Since the present inventors have shown that the abundance of particular microbes in the rumen microbiome is heritable, the present inventors further envisage that it is possible to breed for ruminating animals having particular abundance of microbes in their microbiome. It will be appreciated that this may be carried out without any knowledge as to the trait or purpose which is associated with the inheritable bacteria.

Thus, according to yet another aspect of the present invention there is provided a method of increasing the number of ruminating animals having a desirable microbiome comprising breeding a male and female of said ruminating animals, wherein the rumen microbiome of either of said male and/or said female ruminating animals comprises a hereditable microorganism above a predetermined level, thereby increasing the number of ruminating animals having a desirable microbiome.

Selecting animals having rumen microbiomes which comprise hereditable microbes (e.g. bacteria) can be effected by analyzing samples of rumen microbiomes as further described herein above.

As mentioned, the hereditable microorganism may be associated with a known hereditable trait. Examples of hereditable traits are provided herein above.

Additionally, or alternatively, the hereditable microorganism may affect the relative amount of microbes of the microbiome of the animal (i.e. the overall microbiome composition).

Examples of hereditable microorganisms (e.g. bacteria) are described herein above—e.g. bacteria expressing a 16S rRNA gene sequence selected from the group consisting of SEQ ID NOs: 1-22.

As used herein the term "about" refers to 10%

The terms "comprises" "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes Cellis, J. E., ed. (1994); "Culture of Animal Cells—A Manual of Basic Technique" by Freshney, Wiley-Liss, N. Y. (1994), Third Edition; "Current Protocols in Immunology" Volumes Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL, Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Microbial DNA extraction: The microbial fraction of the rumen fluid was separated following the method of Stevenson and Weimer, 2007, Applied Microbiology and Biotechnology 75:165-174, with the minor modifications that were performed by Jami et al., 2013, The ISME journal 7:1069-1079. DNA was extracted as was described by Stevenson and Weimer (supra).

Genomic DNA extraction: 500 μl of whole blood from each individual animal was mixed with 500 μl Tris-HCl saturated phenol (pH 8.0) and 500 μl of DDW (double distilled water). The mix was shaken for 4 h at room temperature and subsequently centrifuged at 7500 g for 5 min, the aqueous phase was transferred to a new tube with 500 μl of Tris-HCl (pH 8.0) saturated phenol-chloroform (1:1) and subsequently centrifuged at 7500 g for 5 min. The aqueous phase containing the DNA was transferred to a new tube for further processing.

Animal genotyping: The animals are members of the Volcani Center herd of the Agricultural Research Organization, Israel. Within the genotyped animals there were eleven groups each sharing a common sire (groups of half-siblings). One such group consisted of four half-siblings, another consisted of three half-siblings, and all rest of the groups consisted of two half-siblings. Additionally there were two pairs of half-siblings sharing a common dam. There were no full-siblings among the genotyped animals. Genetic relatedness between the cows was assessed solely on their genomic information.

Genomic DNA extractions from the animals where loaded into a Bovine SNP Chip 50K, which is targeted at 54,609 common SNPs that are evenly spaced along the bovine genome (Illumina). The SNP Chip model used was Illumina BovineSNP50-24 v3.0 cat 20000766 and it was processed following manufacturer protocol(Adler et al., 2013, JoVE (Journal of Visualized Experiments):e50683-e50683) at the Genomics Center of the Biomedical Core Facility, Technion, Israel.

16S rRNA sequencing and analysis: Amplification of the 16S V2 region was performed with primers CCTACGG-GAGGCAGCAG (SEQ ID NO: 1; forward) and CCGT-CAATTCMTTTRAGT (SEQ ID NO: 2; reverse). The libraries were then pooled and subsequently sequenced on a single MiSeq flowcell (Illumina) for 251 cycles from each end of the fragments, following analysis with Casava 1.8. A total of 49,760,478 paired end reads were obtained from the total sample, with an average of 106,325 paired end reads per sample. The QIIME pipeline version 1.7.037 was used for data quality control and analyses. OTU analysis was performed on species clusters (97% identity) that were created using UCLUST. OTUs were subjected to Taxonomy assignment using BLAST against the 16S rRNA reference database RDP. Singletons and doubletons were filtered from the dataset, resulting in 85K species with an average of 5,039 per sample.

Genotype data quality control: 47 individuals' genotypes from the current analysis were combined with a reference set of 2,691 individual genotypes that were collected from individual Holstein-Friesian dairy cows in farms all over Israel and Holland (courtesy of the Israeli Cow Breeders Association, ICBA). The reference set of genotypes allowed for a more robust Quality. Control (QC) and for the creation of the generic relationship matrix. QC was performed with the PLINK program, with the following parameters:
-cow --file isgenotype_all --maf 0.05 --geno 0.05 --mind 0.05 -out isgenotype_all_qc --recode12

SNPs that were not genotyped in more than 5% of the individuals were removed. Similarly, individuals were removed from the analysis if they had genotyped in less than 95% of the loci (SNPs) covered by the SNP chip.

354 individuals (one belonging to the study group) were removed because of low genotyping, 3,797 SNPs were removed because of "missingness" in the genotyped populations and 11,290 SNPs failed the MAF criteria. The total number of SNPs passing QC was 40,812.

Generation of genetic relatedness matrix: All animals and SNPs that passed QC were used to generate a matrix that estimates the genetic relatedness between each unique pair of animals. The GCTA (Yang et al. 2011, The American Journal of Human Genetics 88:76-82) software was used to calculate the relationship matrix. The matrix is based on the count of shared alleles, weighted by the allele's rareness:

$$A_{jk} = \frac{1}{N} \sum_{i=1}^{N} \left( \frac{(x_{ij} - 2p_i)(x_{ik} - 2p_i)}{2p_i(1 - p_i)} \right)$$

Where $A_{jk}$ represents the genetic relationship estimate between animals j and k, $X_{ij}$, $X_{ik}$ are the counts of the reference alleles in animals in j and k, respectfully. $P_i$ is the proportion of the reference allele in the population. N is the total number of SNPs used for the relatedness estimation.

Heritability estimates: Heritability estimates of each species were established upon the distribution of the relative abundance of the species under questions in conjunction with the estimated genetic relatedness between the animals. The estimation was performed using the software GCTA. The model used by this software is termed total heritability and reflects the heritability explained all the SNPs that passed QC. The model is:

$$y = X\beta + Wu + \varepsilon$$

where y is the vector of observations (phenotypes). β is a vector of fixed effects (study covariates). X is the design matrix. u is the vector of SNPs effect. W is the standardized genotypes matrix. ε is the individual (residual) effect.

Then the variance in the model could be attributed to two sources, genetic and random error, in the following manner:

$$V = WW'\sigma_u^2 + I\sigma_\varepsilon^2$$

where V is the overall variance. I is the identity matrix (n*n).

$$\sigma_u^2$$

is the variance due to genetics (overall SNP effects).

$$\sigma_\varepsilon^2$$

is the variance due to individual effects (residual). Next, GCTA estimates the value of $$\sigma_u^2$$

and $$\sigma_g^2$$

and the heritability is then estimated as:

$$h^2 = \frac{\sigma_u^2}{\sigma_u^2 + \sigma_\varepsilon^2}$$

Comparing phylogenetic distance within heritable bacterial OTUs to those within overall rumen microbiome: DNA similarity (in percent) between each unique pair within the 22 heritable bacterial OTUs was calculated using clustalw2 (44), and the mean of these similarities was than calculated. A reference range of mean similarities was calculated by randomly sampling 100 subsets of same size each (n=22) drawn from the pool of OTUs appearing in at least 12 genotyped animals (9K). Pairwise DNA similarities and their mean were calculated for each random subset. To draw significance for the mean similarity within the group of heritable bacterial OTUs, its mean similarity was ranked within all 100 mean similarity values that were obtained from the random subsets. OTC correlation odds-ratio:

$$\frac{hc/hn}{nc/nn}.$$

Where hc is the count of heritable OTUs correlated to the index, hn is the count of heritable OTUs not correlated to the index, nc is the count of non-heritable OTUs correlated to the index and nn is the count non-heritable OTUs not correlated to the index. In this context, OTU was correlated to the index if it had a nominal spearman p<0.05.

Statistics and plots: Statistical analysis was performed using R software and plots were produced using the ggplot2 and pheatmap packages.

Experimental design: The main goal was to identify microbial species where significant proportions of their variation in abundance profiles can be attributed to heritable genetic factors. To achieve this, the present inventors analyzed commons SNPs genotyping information of 47 milking Holstein cows. This information was consolidated with additional data for these animals from a recent study (Kruger et al., 2016, ISMS: J 10:2958-2972). For each animal, the 16S rRNA gene was sequenced from samples of three consecutive days. Rumen metabolites were also quantified and rumen metabolic activity assays such as ex-vivo rumen methane production and fiber digestion measurements were performed. Metadata of individual cows' production indices and physiological indices were consolidated. Low quality and non-informative SNPs were removed using a QC pipeline (see material and methods). 16S amplicon sequencing analysis was performed using QIIME pipeline. The rumen microbiome taxonomic profiles represented by 85K species level OTUs (three samples per animal) were associated with genomic data represented by genotyping of common SNP loci (see Methods). Notably, the present inventors focused on identification of heritable microbial OTUs rather than the heritability estimates magnitude. This approach is more robust to heritability estimates values that are typical with small sample sizes in estimation procedure. The microbial OTUs found to be associated to the animals' genomes were further correlated to metabolomics data of the microbiomes, as well as to animal physiology and productivity parameters.

Results

Heritable Species Have High Phylogenetic Relatedness and Are Enriched With the Order Bacteroidales The first step in the present analysis was to identify heritable bacterial species i.e. microbial species where significant proportions of their variation in abundance profiles can be attributed to heritable genetic factors. This would be reflected by a highly similar abundance of certain species among animals that share a similar genetic background. Accordingly, the relatedness between all pairs of animals in the cohort was estimated. This estimation was done by considering both the count and the infrequency of the alleles (SNPs) in the reference genotypes. These pairwise genetic relationship estimates were used together with each species' abundance profile to calculate their heritability estimate.

Figure 6:
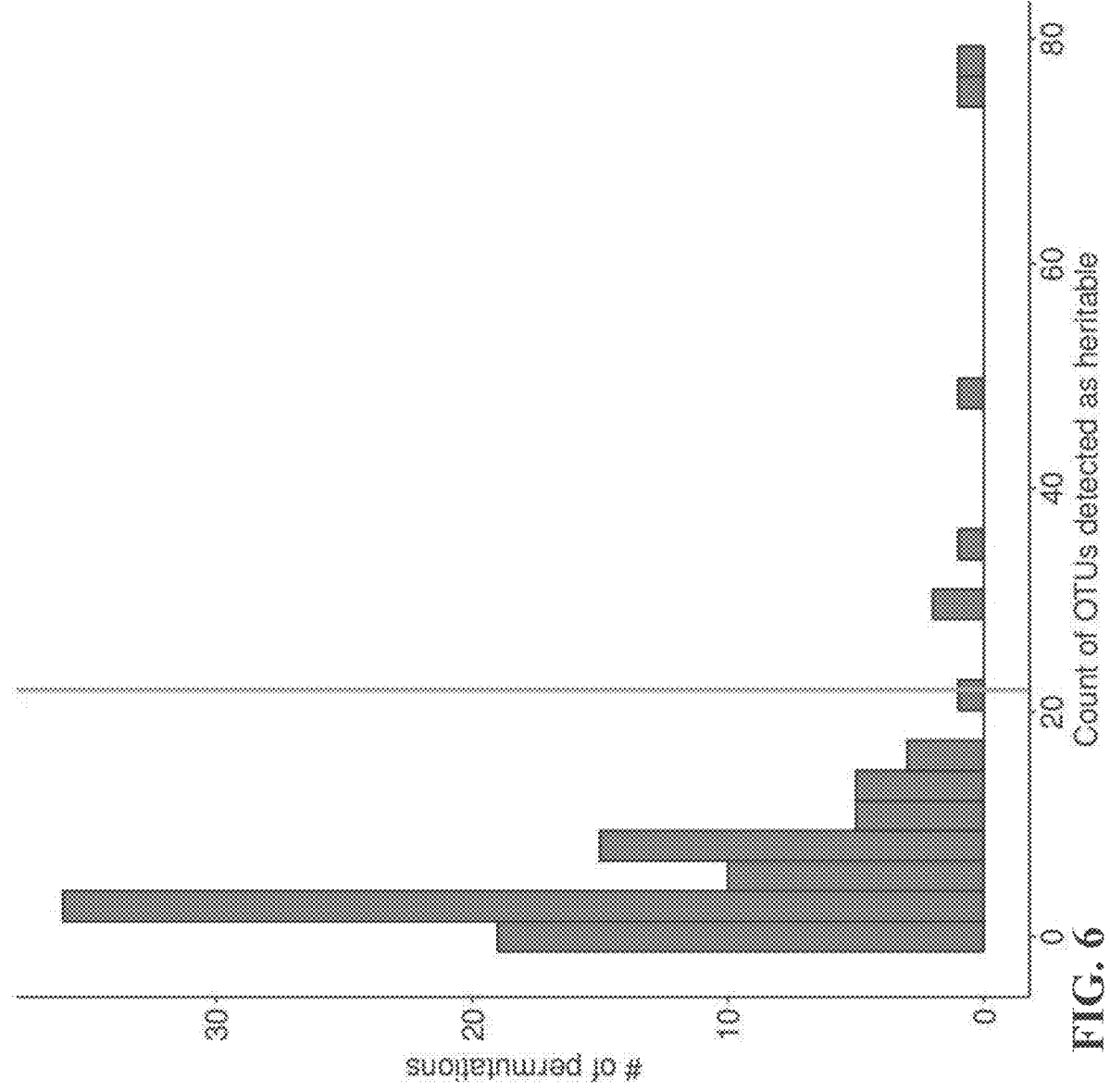
FIG. 6: A histogram showing the false discovery rate the heritability test under permuted assumptions, based on 1.00 random permutations. X-Axis: number of heritable OTUs detected. Y-Axis: number of permutations. A red vertical line presents the number of OTUs detected as heritable in the actual (non-permuted) data.
Figure 7:
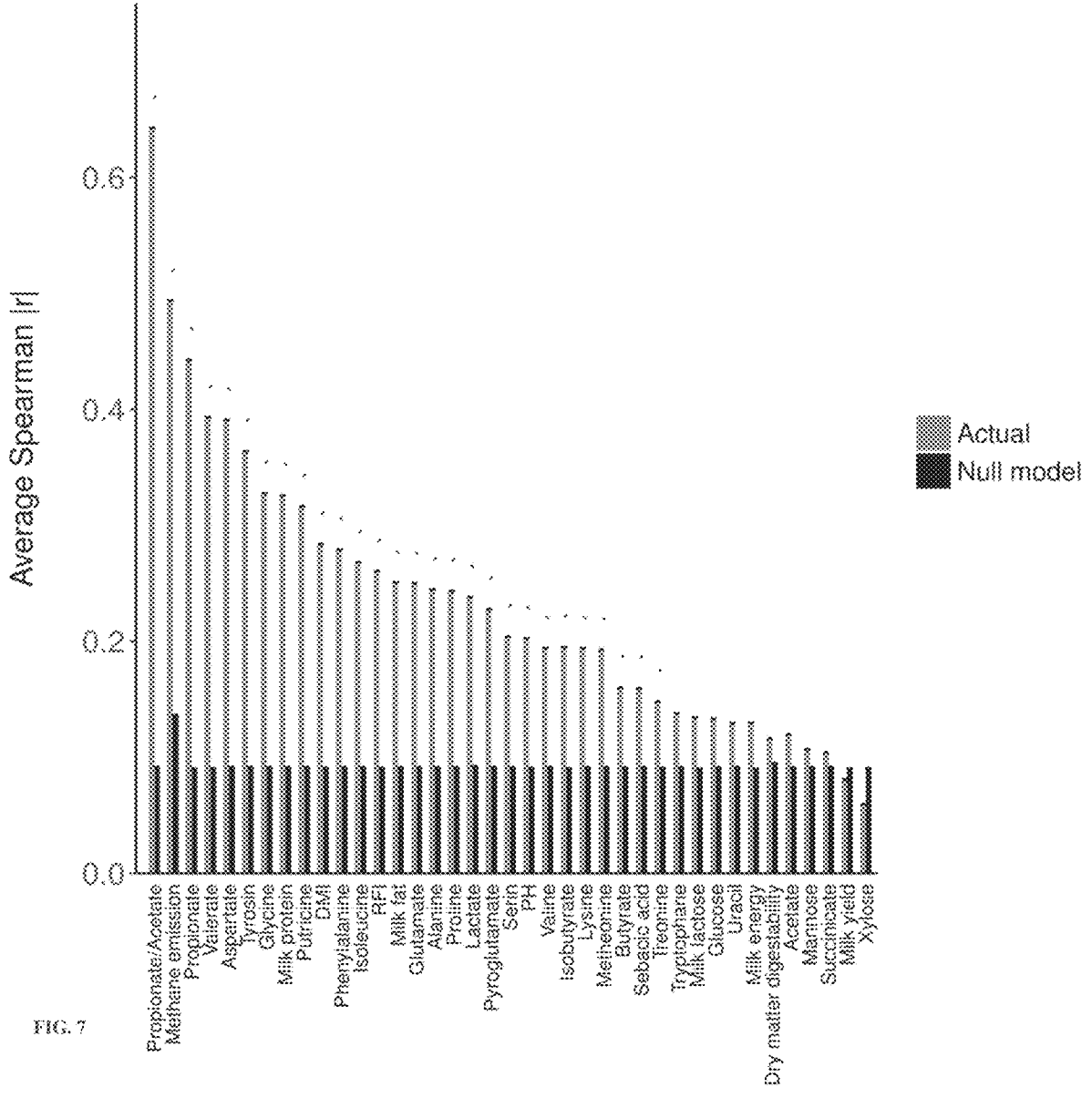
FIG. 7: A null-model for testing the significance of the actual Spearman correlation r values of the heritable OTUs to each of the indices. Red bars represent values resulting from the actual heritable OTUs' relative abundance profile; black bars represent the values derived from 1,000 permutations. In each such permutation each OTU's abundance profile was randomly shuffled.

To increase the confidence of this analysis, the heritability analysis was limited exclusively to OTUs which were present in at least 12 genotyped animals, (25% of the genotyped subset) as previously described (Benson A K et al, 2010, Proceedings of the National Academy of Sciences 107: 18933-18938). In addition, three independent heritability analyses were performed for each OTU, one for each sampling day. Only OTUs that exhibited a significant heritable component (heritability estimate of >0.7 and p-value <0.05) in all three individual sampling days, were considered as heritable OTUs. Following this procedure, the analysis resulted with 22 heritable OTUs that match these criteria (FIG. 8), all belonging to the bacterial domain. Though the heritability significance assessment procedure is based on a parametric test, the present inventors nevertheless inspected the robustness of this finding by examining the false discovery rate distribution of the test under permuted assumptions. For that purpose, they generated a null model with 100 iterations, where in each iteration they repeated the heritability analyses after randomly shuffling the genetic profiles order. In 94% of the permutations the number of OTUS detected as heritable was smaller than 22, while in most permutations the number of OTUs detected as heritable was under 5 (FIG. 6).

Figure 2:
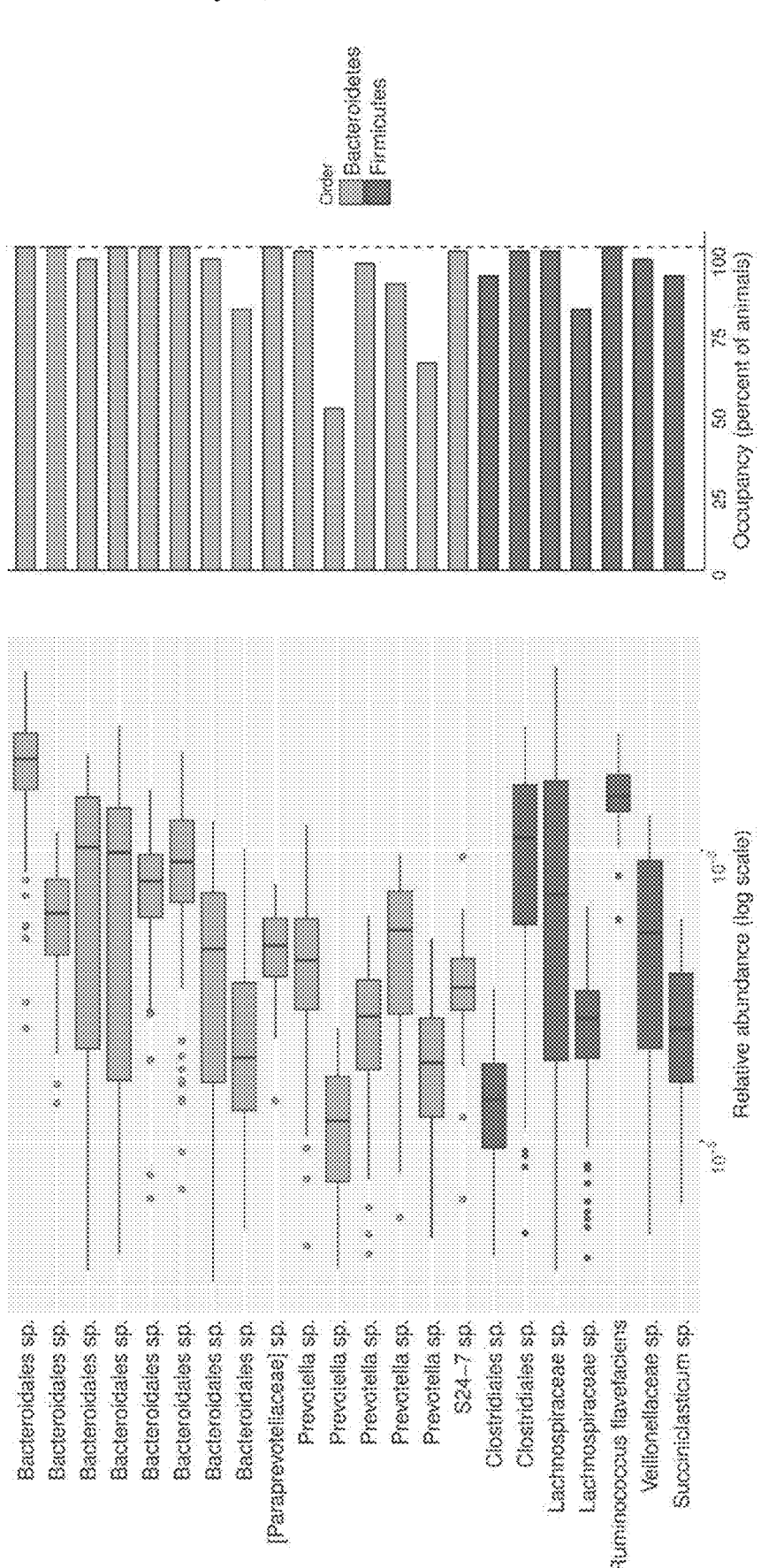
FIG. 2: Heritable OTUs show high presence. OTUs with their taxonomy annotations are listed on the left. The relative abundance of each OTU along the cohort of cows is presented in the left panel, and the presence of each OTU is displayed on the right panel. Green designates an OTU from the Bacteroidales order while brown designates an OTU from the Clostridiales order.
Figure 9:
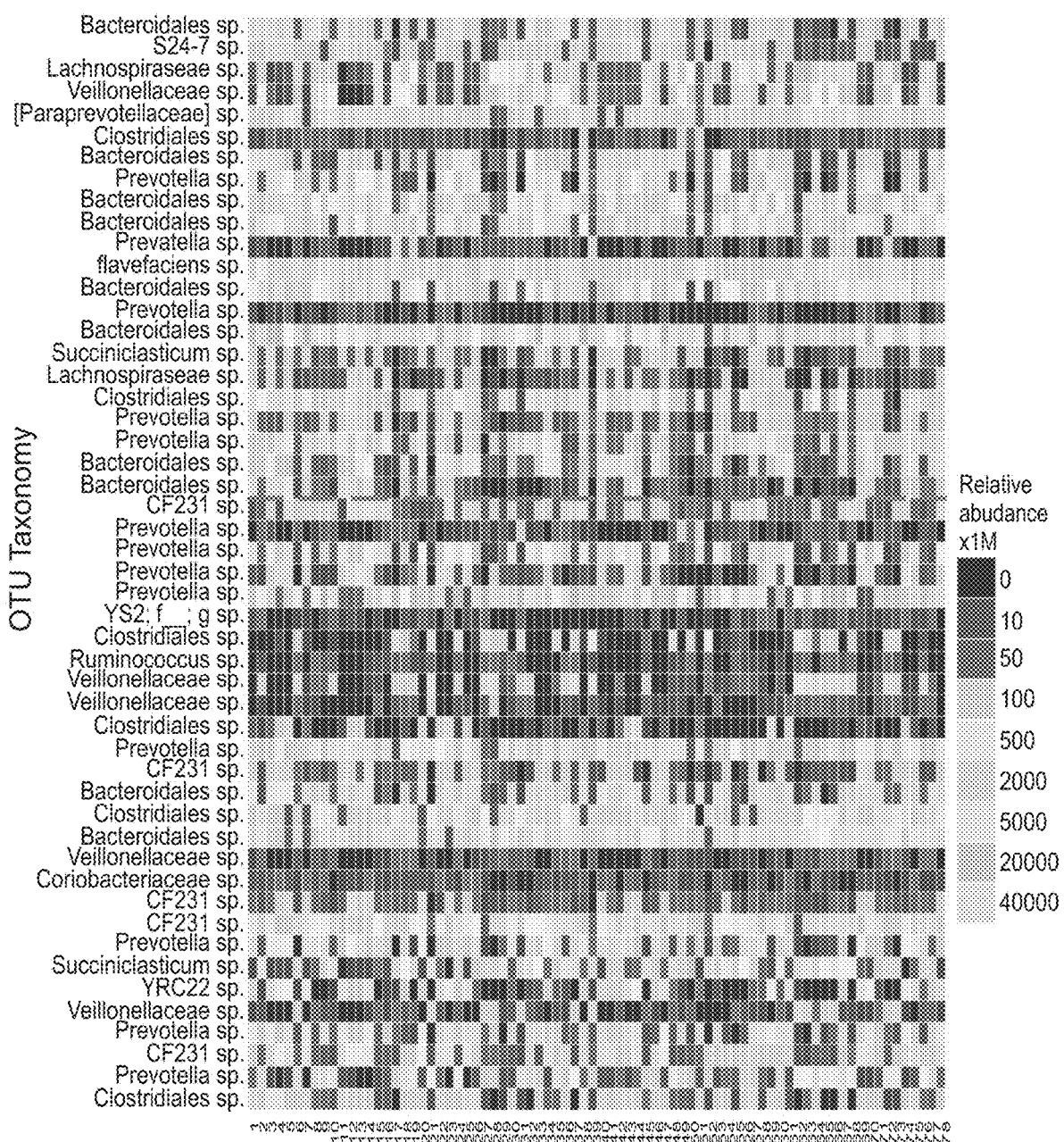
FIG. 9: A heatmap depicting the abundance profiles of heritable microbial OTUs (mean of three sampling days) along the entire study cohort. X-Axis: animal identification number in the experiment. Y-Axis: Taxonomy of microbial OTUs. The heatmap is colored according to the relative abundance of the given OTU in the given animal. Relative abundance is multiplied by 1M to ease readability. Red horizontal line signifies threshold above which OTUs were considered heritable.
Figure 10:
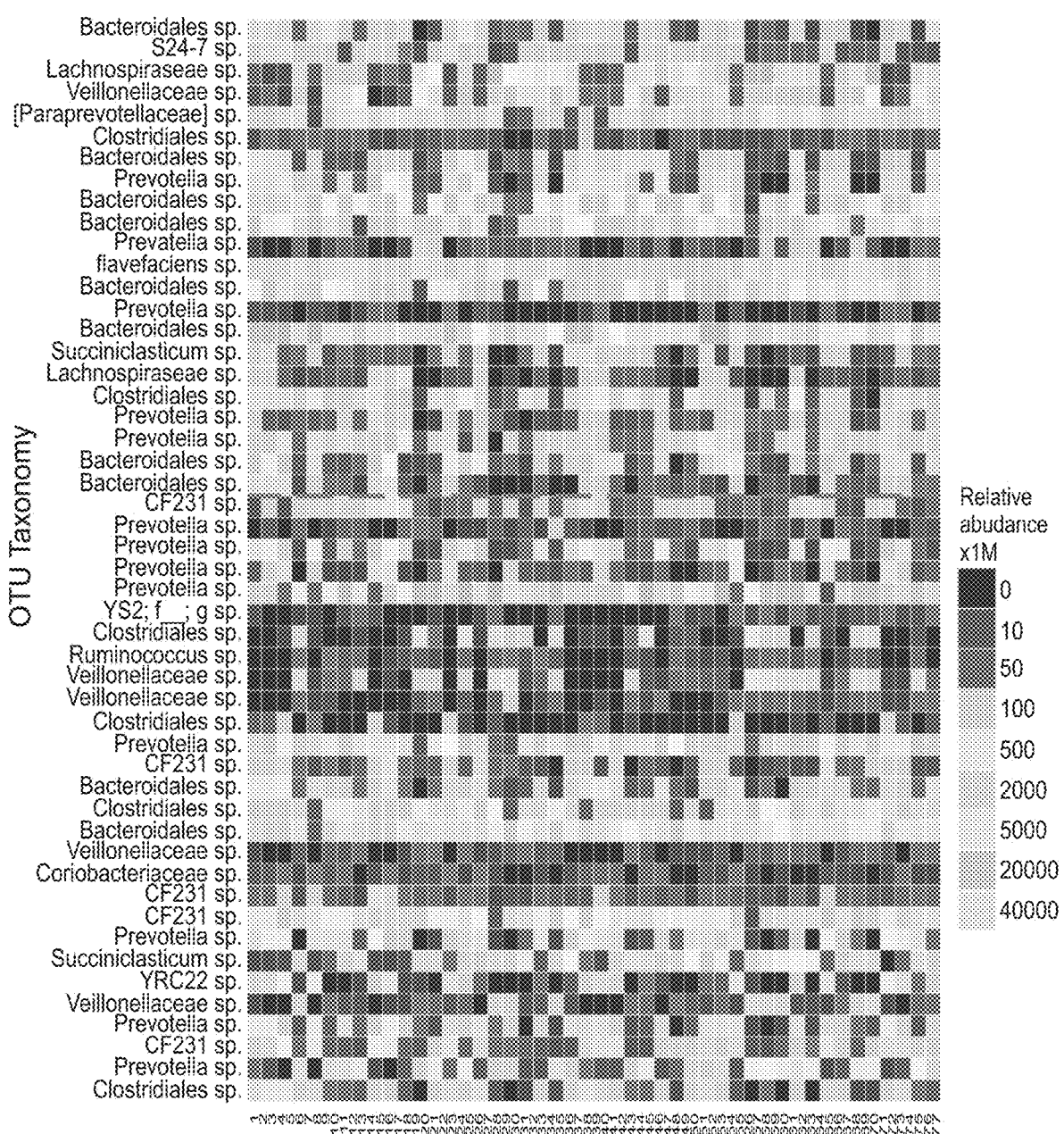
FIG. 10: A heatmap depicting the abundance profiles of heritable microbial OTUs (mean of three sampling days) along the genotyped subset of the study cohort. X-Axis: animal identification number in the experiment. Y-Axis: microbial OTU taxonomy. The heatmap is colored according to the relative abundance of the given OTU in the given animal. Relative abundance is multiplied by 1M to ease readability. Red horizontal line signifies threshold above which OTUs were considered heritable.

It is interesting to note that the heritable OTUs exhibited high presence across animals, ranging between 50%-100% of the animals with the majority appearing in 70 to 100% of the examined animals (FIGS. 2, 9 and 10). The abundance profile of the heritable microbes was correlated to their presence profile (Spearman correlation between the presence counts and abundance sums: r=0.75, p<5×10$^{-5}$).

When the phylogenetic distance was measured between these OTUs, it was found they are highly phylogenetically related on the basis of similarity of their 16S nucleotide sequences (FIG. 1).

These OTUs belong to the two main phyla of the rumen microbiome, namely Bacteroidetes and Firmicutes, and grouped under the two dominant orders in the rumen, Bacteroidales and Clostridiales (FIG. 2).

The present inventors further asked whether this phylogenetic composition of heritable OTUs represents that of the overall species composition in the rumen. It was found that the order Bacteroidales is represented within the heritable OTUs by more species than it is represented in the overall rumen microbiome (trend, Fisher Exact test p<0.053).

Heritable Bacteria Abundance is Correlated to Host Traits as Well as to Rumen Metabolic Parameters and Can Significantly Explain a High Proportion of the Variation Between Animals The present inventors hypothesized that heritable taxa that are correlated to the host genome will potentially be related to rumen metabolism as well as to host physiology. Hence, the present inventors looked for a correlation between heritable microbes and all measured physiological parameters of the animals, as well as to rumen metabolic parameters. In detail, they correlated the abundance profile along the cohort of 78 cows of each heritable OTU to the profile of each measured index (a rumen metabolite or other index). They then compared the mean correlation of heritable OTUs to each of the rumen metabolites and host physiological attributes to a null model. In each of 1,000 iterations of the null model, they shuffled each heritable OTU's abundance profile and recalculated their mean correlation to each of the rumen metabolites and host physiological attributes. This analysis revealed that the heritable OTUs exhibit a strong and significant correlation with many of the rumen metabolic parameters, as well with physiological attributes of the host (FIG. 3, 7).

With relation to rumen metabolism, the strongest correlations for the heritable OTUs was to proionate:acetate ratio (highest magnitude r=0.86, mean |r|=0.64), methane metabolism (highest magnitude r=0.69, mean |r|=0.49), propionic acid (highest magnitude r=−0.6245274, mean |r|=0.44) and valeric acid (highest magnitude r=−0.57, mean |r|=0.39), as well as to the concentration of several amino acids, namely Glycine, Aspartate and Tyrosin (with highest magnitude r=0.51, 0.5, −0.53 and mean |r|=0.32, 0.39, 0.36 respectively). Concerning host attributes, the most correlated parameters were the milk protein (highest magnitude r=0.46, mean |r|=0.33), dry matter intake (highest magnitude r=0.41, mean |r|=0.28) feed efficiency (represented by residual feed intake—RFI, highest magnitude r=0.26, mean |r|=0.39) and milk fat (highest magnitude r=0.39, mean |r|=0.25). Moreover, when the individual correlation of the heritable OTUs to proionate:acetate ratio, methane metabolism, propionic acid and valeric acid were analyzed, it was found that the majority of these OTUs were correlated either positively or negatively to these parameters (FIG. 4A). Regarding host physiological attributes, the majority of heritable OTUs were positively correlated to RFI, DMI and milk protein.

These findings raised the question of whether the portion of heritable microbes that are correlated to host physiology and rumen metabolism is different from the one found in the overall rumen microbiome. To this end the present inventors calculated, for each index, the OTU correlation odds-ratio (see materials and methods), and identified significantly higher odds for an OTU to be correlated to a given index within the heritable microbiome for many parameters. This was especially true for the parameters to which these heritable microbes showed high correlation (FIG. 4B).

Figure 5:
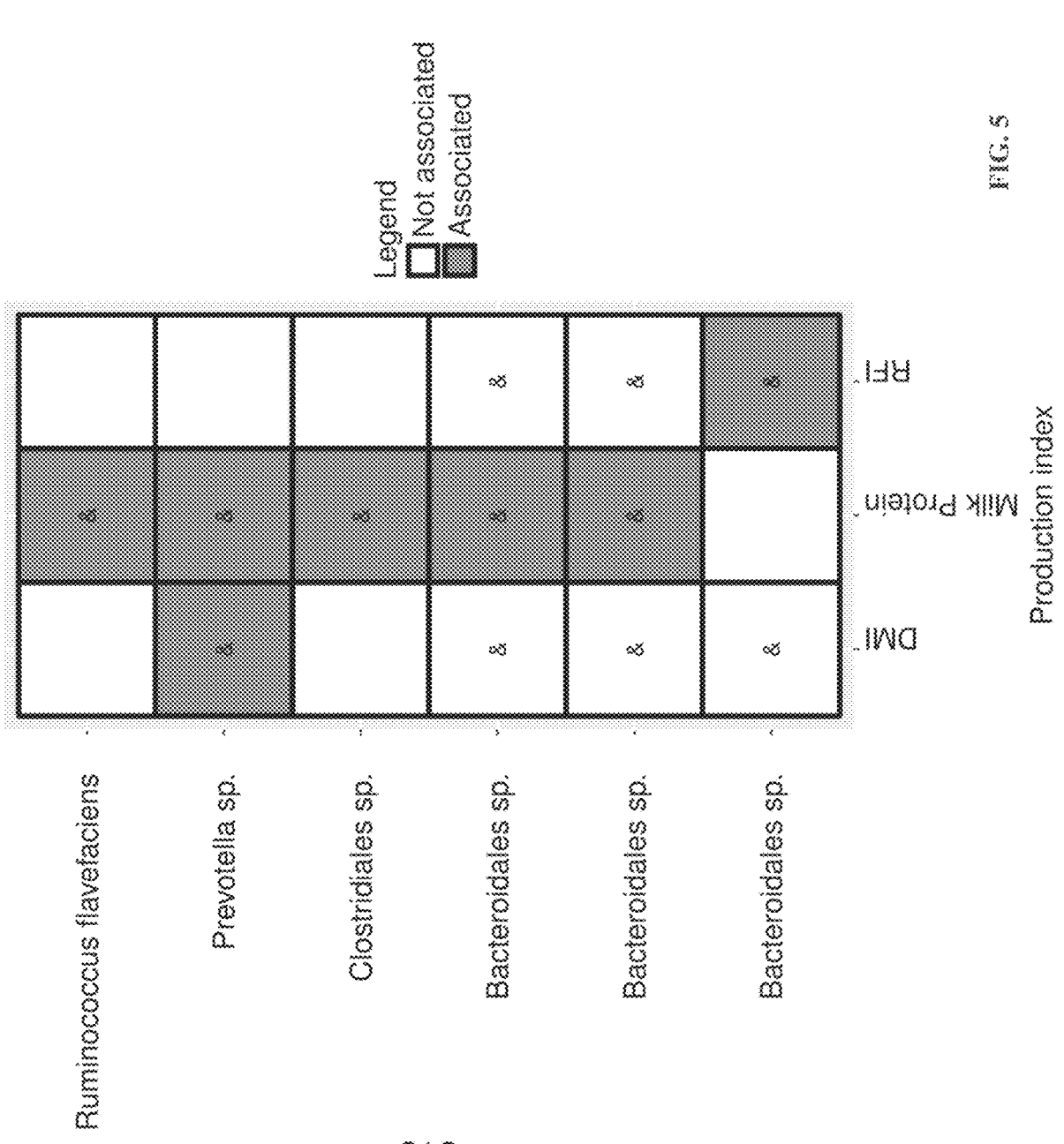
FIG. 5: A portion of heritable OTUs were found to be associated with host physiology in a previous study (Shabat, Sheerli Kruger Ben, et al., ISME J 10:2958-2972, 2016, doi:10.1038/ismej.2016.62). Six of the 22 heritable OTUs that were associated in that study to different cow production indices, namely dry-matter-intake (DMI), milk protein and feed efficiency, measure as residual-feed-intake (RFI). OTUs and their taxonomy are on the rows and the production indices are on the columns. The ampersand symbol inside a tile indicates that a significant correlation was found, in the present examples, between the heritable OTU and the production index.

One of the heritable OTUs with the phylogenetic association of Bacteroidales, which was found to be heritable and highly correlated to the feed efficiency trait in this study, was independently found to be correlated to this trait in a previous study (Kruger Ben Shabat S, et al., 2016. ISME J 10:2958-2972) (FIG. 5). Additionally, five other heritable OTUs with the phylogenetic association of Bacterioidales, Prevotella, Clostridiales and Flavefaciens were found to be highly correlated with milk protein in this study and one OTU of the genus Prevotella mentioned above was also found to be significantly correlated with dry matter intake (DMI) in this previous study (FIG. 5).

Rumen and Animal Physiology Traits Show Varying Heritability Estimates

Figure 11:
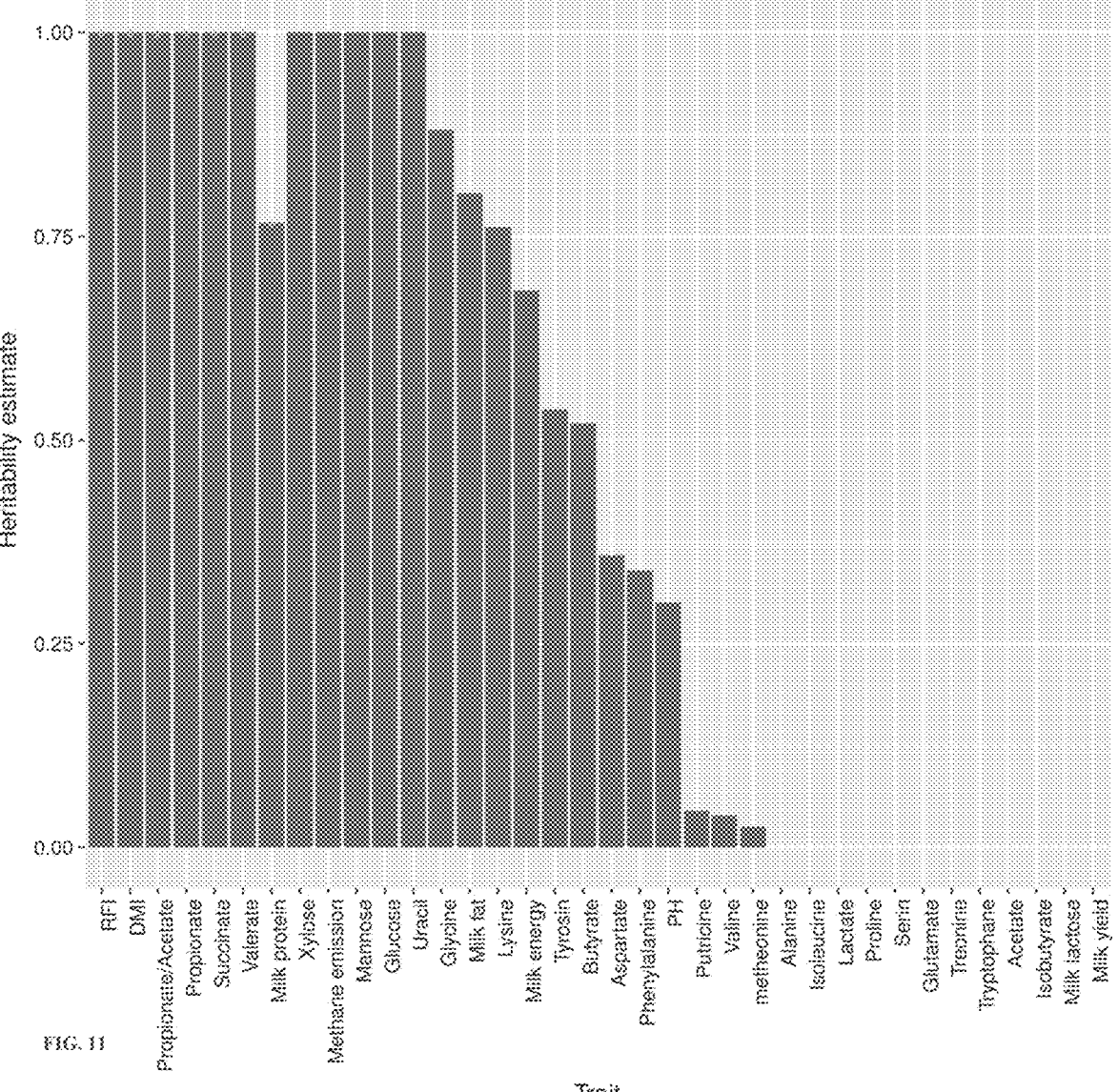
FIG. 11: Heritability estimates of host traits. X-Axis: traits, Y-Axis: Heritability estimate. A star on the top of the bar signifies significant genetic component.

After identifying heritable microbial species that exhibit correlation to host traits, the present inventors set out to estimate heritability of the different important host and rumen metabolism traits with which they found the heritable microbes to be correlated (FIG. 11). The VFAs propionate, succinate and valerate along with milk protein with the efficiency measures of RFI and DMI exhibited significant heritability estimates.

REFERENCES

1. Reyniers J A. 1959. The pure-culture concept and gnotobiotics. Annals of the New York Academy of Sciences 78:3-16.
2. Gilbert J A, Neufeld J D. 2014. Life in a world without microbes. PLoS biology 12:e1002020.
3. Mizrahi I. 2013. Rumen symbioses, p 533-544, The Prokaryotes. Springer.
4. Kittelmann S., Pinares-Patiño C S, Seedorf H, Kirk M R, Ganesh S, McEwan J C, Janssen P H. 2014. Two different bacterial community types are linked with the low-methane emission trait in sheep. PLoS One 9:e103171.
5. Shi W, Moon C D, Leahy S C, Kang D, Froula J, Kittelmann S, Fan C, Deutsch S, Gagic D, Seedorf H. 2014. Methane yield phenotypes linked to differential gene expression in the sheep rumen microbiome. Genome research 24:1517-1525.
6. Ross E M, Moate P J, Marett L C, Cocks B G, Hayes B J. 2013. Metagenomic predictions: from microbiome to complex health and environmental phenotypes in humans and cattle. PLoS one 8:e73056.
7. Wallace R J, Rooke J A, McKain N, Duthie C-A, Hyslop J J, Ross D W, Waterhouse A, Watson M, Roche R. 2015. The rumen microbial metagenome associated with high methane production in cattle. BMC genomics 16:839.
8. Jami E, White B A, Mizrahi I. 2014. Potential role of the bovine rumen microbiome in modulating milk composition and feed efficiency. PLoS One 9:e85423.
9. Carberry C A, Kenny D A, Han S, McCabe M S, Waters S M. 2012. Effect of phenotypic residual feed intake and dietary forage content on the rumen microbial community of beef cattle. Applied and environmental microbiology 78:4949-4958.
10. Mizrahi I. 2012. The role of the rumen microbiota in determining the feed efficiency of dairy cows, p 203-210, Beneficial Microorganisms in Multicellular Life Forms. Springer.
11. Guan L L, Nkrumah J D, Basarab J A, Moore S S. 2008. Linkage of microbial ecology to phenotype: correlation of rumen microbial ecology to cattle's feed efficiency. FEMS Microbiology Letters 288:85-91.

12. McCann J C, Wiley L M, Forbes T D, Rouquette Jr F M, Tedeschi L O. 2014. Relationship between the rumen microbiome and residual feed intake-efficiency of Brahman bulls stocked on bermudagrass pastures. PLoS One 9:e91864.

13. Kruger Ben Shabat S, Sasson G, Doron-Faigenboim A, Dorman T, Yaacoby S, Berg Miller M E, White B A, Shterzer N, Mizrahi I. 2016. Specific microbiome-dependent mechanisms underlie the energy harvest efficiency of ruminants. ISME 10:2958-2972.

14. Fernando S C, Purvis H, Najar F, Sukharnikov L, Krehbiel C, Nagaraja T, Roe B, DeSilva U. 2010. Rumen microbial population dynamics during adaptation to a high-grain diet. Applied and Environmental Microbiology 76:7482-7490.

15. Kim M, Morrison M, Yu Z. 2011. Phylogenetic diversity of bacterial communities in bovine rumen as affected by diets and microenvironments. Folia microbiologica 56:453.

16. Kittelmann S, Janssen P H. 2011. Characterization of rumen ciliate community composition in domestic sheep, deer, and cattle, feeding on varying diets, by means of PCR-DGGE and clone libraries. FEMS Microbiology Ecology 75:468-481.

17. Kocherginskaya S A, Aminov R I, White B A. 2001. Analysis of the rumen bacterial diversity under two different diet conditions using denaturing gradient gel electrophoresis, random sequencing, and statistical ecology approaches. Anaerobe 7:119-134.

18. Tajima K. Aminov R, Nagamine T, Matsui H, Nakamura M, Benno Y. 2001. Diet-dependent shifts in the bacterial population of the rumen revealed with real-time PCR. Applied and environmental microbiology 67:2766-2774.

19. Friedman N, Shriker E, Gold B, Durman T, Zarecki R, Ruppin E, Mizrahi I. 2017. Diet-induced changes of redox potential underlie compositional shifts in the rumen archaeal community. Environmental microbiology 19:174-184.

20. Shaani Y, Eliyahu D, Mizrahi I, Yosef E, Ben-Meir Y, Nikbachat M, Solomon R, Mabjeesh S J, Miron J. 2016. Effect of feeding ensiled mixture of pomegranate pulp and drier feeds on digestibility and milk performance in dairy cows. Journal of Dairy Research 83:35-41.

21. Roche R, Dewhurst R J, Duthie C-A, Rooke J A, McKain N, Ross D W, Hyslop J J, Waterhouse A, Freeman T C, Watson M. 2016. Bovine host genetic variation influences rumen microbial methane production with best selection criterion for low methane emitting and efficiently feed converting hosts based on metagenomic gene abundance. PLoS Genet 12:e1005846.

22. Li Z. Wright A D G, Si H, Wang X, Qian W, Zhang Z, Li G. 2016. Changes in the rumen microbiome and metabolites reveal the effect of host genetics on hybrid crosses. Environmental Microbiology Reports 8:1016-1023.

23. Caporaso J G, Kuczynski J, Stombaugh J, Bittinger K, Bushman F D, Costello E K, Fierer N, Peña A G, Goodrich J K, Gordon J I. 2010. QIIME allows analysis of high-throughput community sequencing data. Nature methods 7:335-336.

24. Benson A K, Kelly S A, Legge R, Ma F, Low S J, Kim J, Zhang M. Oh P L, Nehrenberg D, Hua K. 2010. Individuality m gut microbiota composition is a complex polygenic trait shaped by multiple environmental and host genetic factors. Proceedings of the National Academy of Sciences 107:18933-18938.

25. VanRaden P, Van Tassell C, Wiggans G, Sonstegard T, Schnabel R, Taylor J, Schenkel F. 2009. Invited review: Reliability of genomic predictions for North American Holstein bulls. Journal of dairy science 92:16-24.

26. Williams Y, Pryce J, Grainger C, Wales W, Linden N, Porker M, Hayes B. 2011. Variation in residual feed intake in Holstein-Friesian dairy heifers in southern Australia. Journal of Dairy Science 94:4715-4725.

27. Benson A K. 2016. The gut microbiome—an emerging complex trait. Nature genetics 48:1301-1302.

28. Felsenstein J. 1985. Phylogenies and the comparative method. The American Naturalist 125:1-15.

29. Ungerfeld E M, Rust S R, Burnett R. 2003. Use of some novel alternative electron sinks to inhibit ruminal methanogenesis. Reproduction Nutrition Development 43:189-202.

30. Öztürk M. 1991. Conversion of acetate, propionate and butyrate to methane under thermophilic conditions in batch reactors. Water Research 25:1509-1513.

31. Bryant M. 1979. Microbial methane production theoretical aspects. Journal of Animal Science 48:193-201.

32. Kamke J, Kittelmann S, Soni P, Li Y, Tavendale M, Ganesh S, Janssen P H, Shi W, Froula J, Rubin E M. 2016. Rumen metagenome and metatranscriptome analyses of low methane yield sheep reveals a Sharpen-enriched microbiome characterised by lactic acid formation and utilisation. Microbiome 4:56.

33. Rogers J, Peirce-Sandner S, Papas A, Polan C, Sniffen C, Muscato T, Staples C, Clark J. 1989. Production responses of dairy cows fed various amounts of rumen-protected methionine and lysine. Journal of dairy science 72:1800-1817.

34. Stevenson D M, Weimer P J. 2007. Dominance of Prevotella and low abundance of classical ruminal bacterial species in the bovine rumen revealed by relative quantification real-time PCR. Applied Microbiology and Biotechnology 165:174.

35. Jami E, Israel A, Kotser A, Mizrahi I. 2013. Exploring the bovine rumen bacterial community from birth to adulthood. The ISME journal 7:1069-1079.

36. Ron M, Blanc Y, Band M, Ezra E, Weller J. 1996. Misidentification rate in the Israeli dairy cattle population and its implications for genetic improvement. Journal of Dairy Science 79:676-681.

37. Adler A J, Wiley G B, Gaffney P M. 2013. Infinium assay for large-scale SNP genotyping applications. JoVE (Journal of Visualized Experiments):e50683-e50683.

38. Edgar R C. 2010. Search and clustering orders of magnitude faster than BLAST. Bioinformatics 26:2460-2461.

39. Altschul S F, Gish W, Miller W, Myers E W, Lipman D J. 1990. Basic local alignment search tool. Journal of molecular biology 215:403-410.

40. Cole J R, Wang Q, Cardenas E, Fish J, Chai B, Farris R J, Kulam-Syed-Mohideen A, McGarrell D M, Marsh T, Garrity G M. 2009. The Ribosomal Database Project: improved alignments and new tools for rRNA analysis. Nucleic acids research 37:D141-D145.

41. Purcell S, Neale B, Todd-Brown K, Thomas L, Ferreira M A, Bender D, Mailer J, Sklar P, De Bakker P I, Daly M J. 2007. PLINK: a tool set for whole-genome association and population-based linkage analyses. The American Journal of Human Genetics 81:559-575.

42. Yang J, Lee S H, Goddard M E, Visscher P M. 2011. GCTA: a tool for genome-wide complex trait analysis. The American Journal of Human Genetics 88:76-82.
43. Yang J, Benyamin B, McEvoy B P, Gordon S, Henders A K, Nyholt D R, Madden P A, Heath A C, Martin N G, Montgomery G W. 2010. Common SNPs explain a large proportion of the heritability for human height. Nature genetics 42:565-569.
44. Larkin M A, Blackshields G, Brown N, Chenna R, McGettigan P A, McWilliam H, Valentin F, Wallace I M, Wilm A, Lopez R. 2007. Clustal W and Clustal X version 2.0. bioinformatics 23:2947-2948.
45. Team R C. 2016. R: A language and environment for statistical computing. Vienna: R Foundation for Statistical Computing; 2014.
46. Wickham H. 2016. ggplot2: elegant graphics for data analysis. Springer.
47. Kolde R. 2015. pheatmap: Pretty Heatmaps. R package version 1.0.2.

What is claimed:

1. A method of breeding cows comprising:

selecting a male cow having a rumen microbiome which comprises bacteria which express a 16S rRNA gene sequence selected from the group consisting of SEQ ID NOs: 15, 19 and 21, wherein presence of said bacteria is statistically associated with methane production of less than 100 g per day in the selected male cow; and breeding said male cow with a female cow.

2. The method of claim 1, wherein said cows comprise Holstein-Friesian cows.

3. A method of using a male cow for breeding, the method comprising:

(a) analyzing a rumen microbiome sample of a male cow for the presence of bacteria which express a 16S rRNA gene sequence selected from the group consisting of SEQ ID NOs: 15, 19 and 21, wherein presence of said bacteria is indicative of a methane production of less than 100 g per day in the male cow;

(b) selecting the male cow which shows the presence of said bacteria;

(c) obtaining semen from said selected male cow; and (d) inseminating a female cow with said semen, thereby using the male cow for breeding.

4. The method of claim 3, further comprising analyzing methane production and/or feed efficiency in the offspring.

5. The method of claim 3, wherein said cows comprise Holstein-Friesian cows.

* * * * *